United States Patent
Harkins, Jr.

(10) Patent No.: US 11,723,870 B1
(45) Date of Patent: Aug. 15, 2023

(54) ASSEMBLY, APPARATUS AND METHOD FOR LYOPHILIZATION

(71) Applicant: Thomas John Harkins, Jr., Whaleyville, MD (US)

(72) Inventor: Thomas John Harkins, Jr., Whaleyville, MD (US)

( * ) Notice: Subject to any disclaimer, the term of this patent is extended or adjusted under 35 U.S.C. 154(b) by 0 days.

(21) Appl. No.: 18/066,107

(22) Filed: Dec. 14, 2022

Related U.S. Application Data

(63) Continuation-in-part of application No. 17/588,349, filed on Jan. 31, 2022, now Pat. No. 11,536,512.

(60) Provisional application No. 63/474,132, filed on Jul. 21, 2022.

(51) Int. Cl.
*A61K 9/19* (2006.01)
*F26B 5/06* (2006.01)

(52) U.S. Cl.
CPC . *A61K 9/19* (2013.01); *F26B 5/06* (2013.01)

(58) Field of Classification Search
CPC ... A47K 9/19; F26B 5/06; F26B 25/18; F26B 25/008; A61J 1/14
USPC ..................................................... 34/284, 92
See application file for complete search history.

(56) References Cited

U.S. PATENT DOCUMENTS

| | | |
|---|---|---|
| 3,795,986 A | 3/1974 | Sutherland |
| 3,817,259 A | 6/1974 | Strasser |
| 4,127,947 A | 12/1978 | Webb |
| 5,286,448 A | 2/1994 | Childers |
| 5,522,155 A | 6/1996 | Jones |
| 5,596,814 A | 1/1997 | Zingle |
| 5,964,043 A | 10/1999 | Oughton |
| 6,122,836 A | 9/2000 | Tenedini |
| 6,199,297 B1 | 3/2001 | Wisniewski |
| 6,290,680 B1 * | 9/2001 | Forsberg ................. A61M 5/24 141/237 |

(Continued)

FOREIGN PATENT DOCUMENTS

| | | |
|---|---|---|
| GB | 1011475 | 12/1965 |
| JP | 2012046250 | 3/2012 |

(Continued)

OTHER PUBLICATIONS

Butler, CA, Mccullough RL, Pitchumani R., Gillespie JW, "An Analysis of Mechanisms Governing Fusion Bonding of Thermoplastic Composites", *Journal of Thermoplastic Composite Materials*, Jul. 1998, vol. 11(4):338-363.

(Continued)

*Primary Examiner* — Stephen M Gravini
(74) *Attorney, Agent, or Firm* — Smith Patent, LLC; Chalin A. Smith

(57) ABSTRACT

Herein described are an assembly, apparatus and method for lyophilization that utilizes a thermal block made from a conductive material, the block having multiple wells designed and dimensioned to receive containers carrying material to be lyophilized in situ. In preferred embodiments, a vented silicone pad covers the wells and secures the containers therein, and a similarly vented rigid plate in turn secures the silicone pad by fastening it to the thermal block. The assembly can be turned up to 90 degrees resulting in the turning of the containers from an upright position to a horizontal position, a position in which the distance through which sublimation must progress is drastically reduced so as to greatly enhance the efficiency of the lyophilization process.

20 Claims, 37 Drawing Sheets

(56) References Cited

U.S. PATENT DOCUMENTS

| | | |
|---|---|---|
| 7,086,177 B2 | 8/2006 | Alstat |
| 9,005,183 B2 | 4/2015 | Harkins |
| 9,222,728 B2 | 12/2015 | Py |
| 9,435,586 B2 | 9/2016 | Ling |
| 9,739,532 B2 | 8/2017 | Baugh |
| 10,364,053 B2 | 7/2019 | Wensley |
| 10,443,935 B2 * | 10/2019 | Knight .................. B01L 9/06 |
| 11,536,512 B1 * | 12/2022 | Harkins, Jr. .............. F26B 9/06 |
| 2009/0001042 A1 | 1/2009 | Sever |
| 2014/0183094 A1 | 7/2014 | Imai |
| 2018/0044076 A1 * | 2/2018 | Eichhorn .............. A61J 1/1406 |
| 2018/0110922 A1 | 4/2018 | Dunki-Jacobs |
| 2020/0223604 A1 | 7/2020 | Heinlein |
| 2022/0110829 A1 | 4/2022 | Zwimmann |

FOREIGN PATENT DOCUMENTS

| | | | |
|---|---|---|---|
| WO | WO-9527180 | 10/1995 | |
| WO | WO-9915215 A1 * | 4/1999 | .............. A61J 1/062 |
| WO | WO-2016153476 A1 * | 9/2016 | ............ A61J 1/1406 |
| WO | WO-2019063772 | 4/2019 | |

OTHER PUBLICATIONS

Coogan, Timothy J., Kazmer, David O., "Modeling of interlayer contact and contact pressure during fused filament fabrication", *Journal of Rheology*, Jul. 1, 2019, vol. 63 (4): 655-672.

* cited by examiner

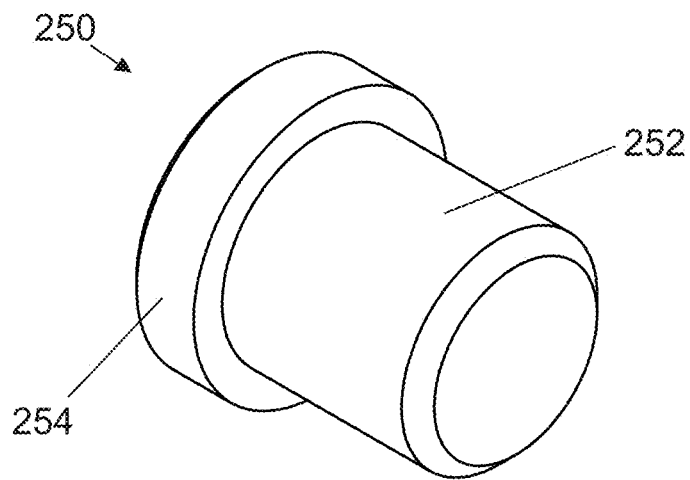
Fig. 13
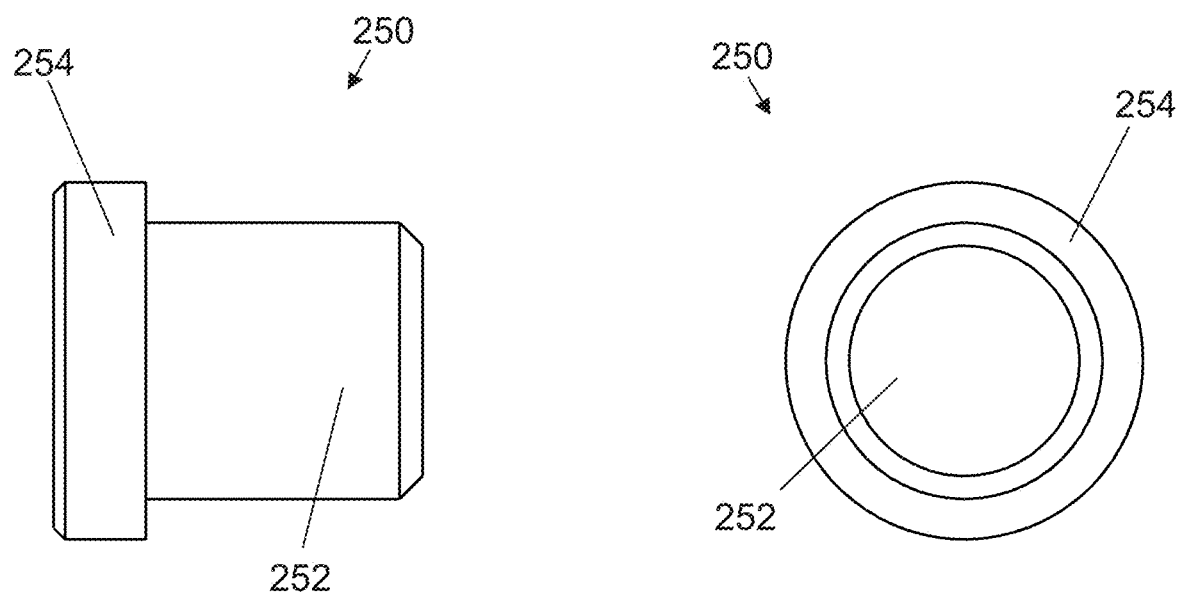
Fig. 14
Fig. 15

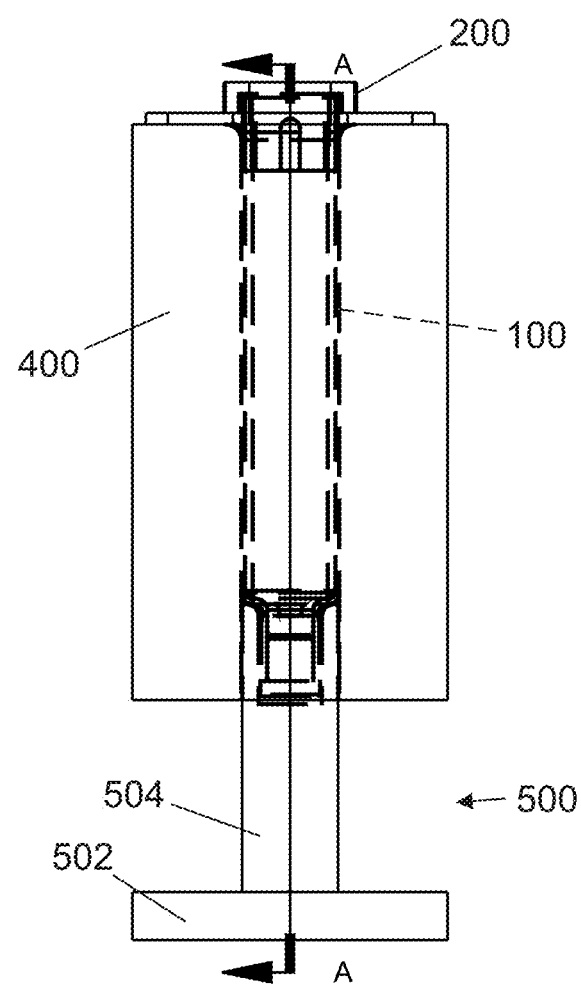 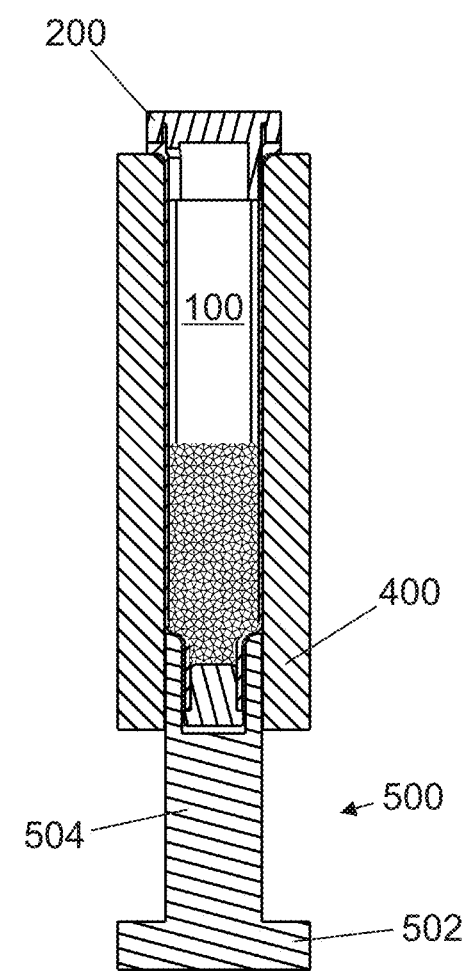
Fig. 54
Fig. 55

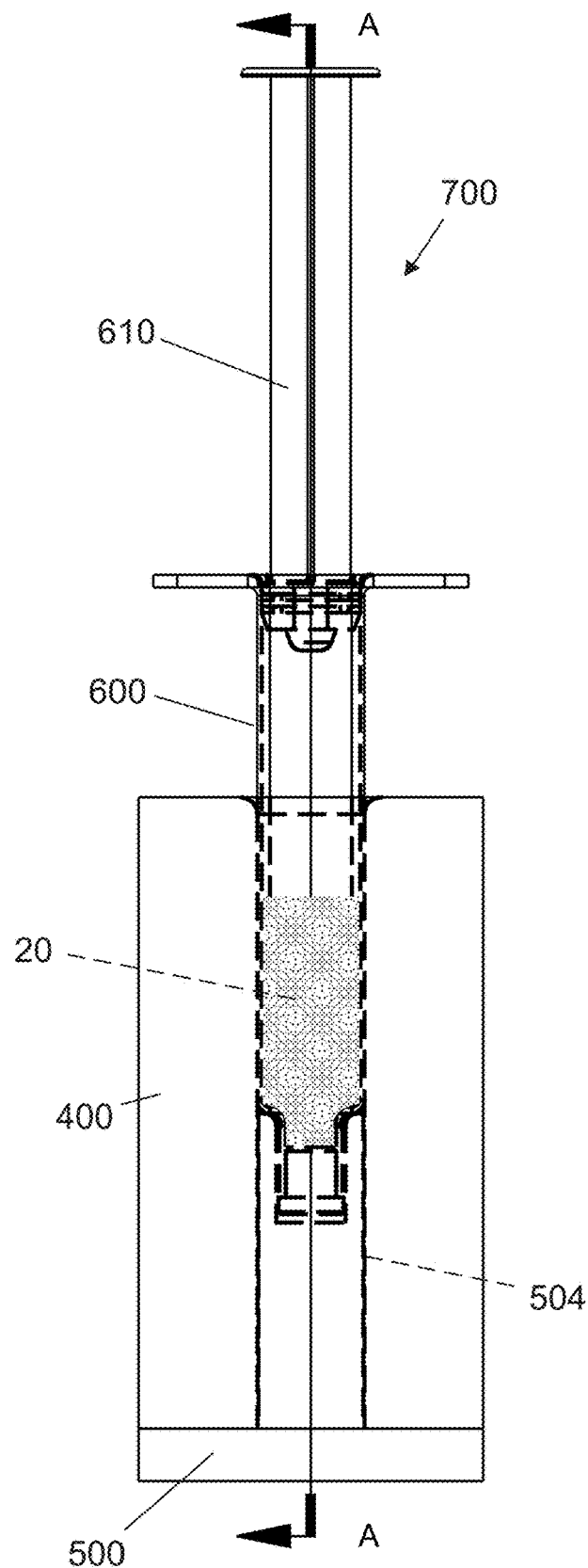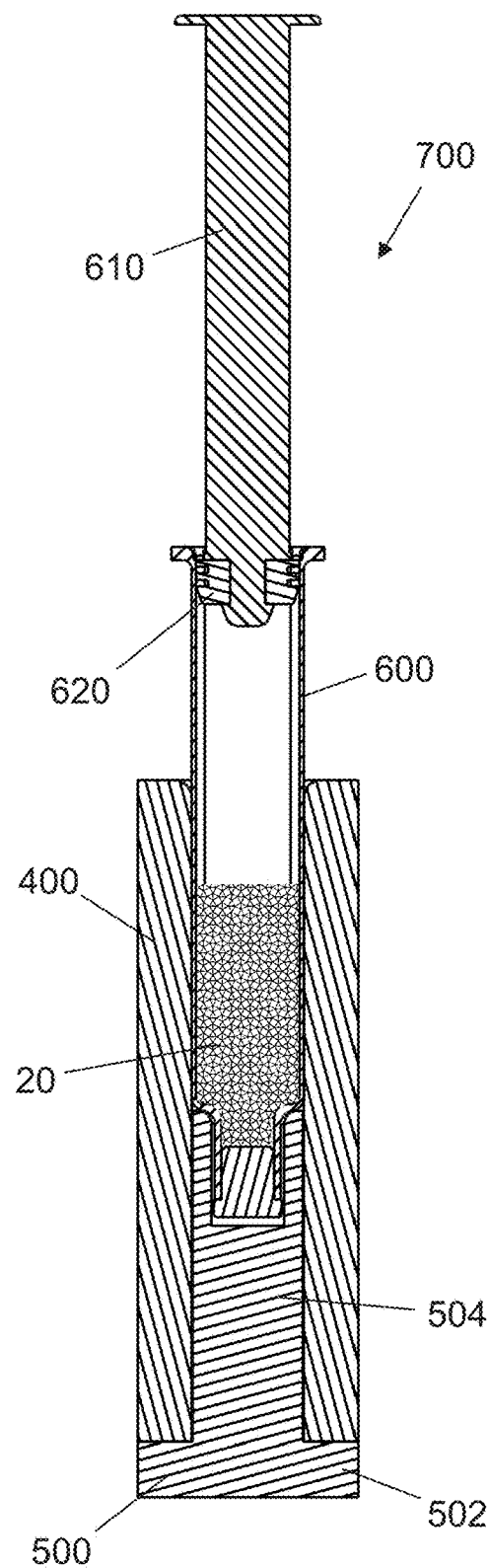
Fig. 73
Fig. 74

ASSEMBLY, APPARATUS AND METHOD FOR LYOPHILIZATION

I. PRIORITY

This application is a continuation-in-part of U.S. patent application Ser. No. 17/588,349 filed Jan. 31, 2022, which issued as U.S. Pat. No. 11,536,512 on Dec. 27, 2022, the contents of which are hereby incorporated by reference in their entirety. This application also claims the benefit of U.S. Provisional Application No. 63/474,132 filed Jul. 21, 2022, the contents of which are hereby incorporated by reference in their entirety.

II. TECHNICAL FIELD

The present invention relates to an assembly, apparatus and method for lyophilization. More particularly, the present invention relates to an improved assembly, apparatus and method for lyophilization of materials, particularly biological preparations including but not limited to pharmaceuticals.

III. BACKGROUND OF THE PRESENT INVENTION

Freeze-drying, also known as lyophilization or cryodessication, is a well-known low temperature dehydration process universally accepted across multiple industries, including the chemical, pharmaceutical, and food industries, that involves freezing a product (typically a liquid or water-containing product), lowering pressure, then removing the ice via sublimation. This stands in contrast to the more conventional dehydration processes that use heat to evaporate water in its liquid form.

Primary applications of lyophilization include biological (e.g., bacteria and yeasts), biomedical (e.g., surgical transplants, pharmaceuticals), food processing (e.g., coffee) and preservation. Due to the low temperature used in processing, the quality of the lyophilized product upon rehydration is excellent. Lyophilized products further offer certain advantages such as extended shelf-life and stability which makes the process popular.

The process of lyophilization has been widely adopted in the pharmaceutical industry and more specifically in biological preparations. Most biological preparations are temperature sensitive and have a short shelf life. Other biological formulations, such as vaccines, need to be stored at temperatures as low as −70 to −80° C. or below. Indeed, a first iteration of the Pfizer-BioNTech COVID-19 vaccine required storage at ultra-low freezing temperatures, about −100 degrees Fahrenheit, a temperature that falls well below standard freezer capabilities.

Equipment to maintain such low temperature for storage and transportation is expensive and often not available. Lyophilized formulations, however, have less temperature stringency and can therefore be stored at temperatures above 0° C. that can be easily maintained in normal refrigerators. Additionally, the lyophilized formulations have a long shelf life, and the dosage remains within pharmaceutical specifications for a longer time. The lyophilized dosage forms can be readily solubilized for easy and dependable administration. This improved stability, extended shelf life, and minimal refrigeration and monitoring requirements during transit and storage make lyophilization processes exceptionally well-suited for preserving and storing biological preparations.

Lyophilization has traditionally been performed in containers, such as vials and ampoules. Lyophilization can also be performed directly in a syringe, with the lyophilized medication being stored in the same syringe. However, convection and radiation, the most common methods for heat transfer in the lyophilization process, are slow processes that tend to be associated with non-uniform heating during batch lyophilization. For example, under typical radiation condition, uneven heat transfer gives rise to higher sublimation rates in those vials or syringes located on the periphery of an array (e.g., at the front and sides of the array) as compared to those more centrally disposed. To wit, it is quite common for a batch to have fully mature hard product cake at the edges of the pan while the center of the batch is soft and raw. This lack of uniformity is highly problematic.

However, pharmaceuticals lyophilized directly in a dispensing syringe are highly preferred for their stability and long shelf life, as well as their convenience. For example, at patient administration, a diluent can be added to the pre-filled syringe for reconstitution of the lyophilized product, thereby allowing the medication to be administered from the lyophilized syringe directly to the patient. Such in-situ lyophilization also reduces labor as compared to preparation of a patient injection from a vial. In addition, product waste is reduced, while a more accurate dosage is administered. As vaccines provided in multidose vials wane in demand and the single-dose vaccine becomes more preferred, lyophilized medicines are uniquely positioned by not requiring the burden of ultra-low temperature freezing for shipment, storage, and product monitoring by expensive temperature sensing systems requiring remote 24/7 surveillance on the product.

Considering the benefits afforded by lyophilization as well as its increasing use in industry, there remains a constant desire, particularly in the pharmaceutical arts, to make the lyophilization process more efficient by reducing the product lyophilization cycle timeline, increasing throughput making the process more economical.

IV. SUMMARY OF THE PRESENT INVENTION

Bearing in mind the above, the present invention offers an improvement over the state of the art by utilizing an apparatus and methodology whereby lyophilization cycles can be shortened using novel design techniques and materials.

Accordingly, it is a primary objective of the present invention to provide a lyophilization assembly, apparatus and method that imparts a shorter lyophilization cycle timeline. It is another objective of the present invention that the lyophilization method be efficient. It is still another objective of the present invention to provide a readily scalable lyophilization apparatus and method. It is yet a further objective of the present invention to provide a lyophilization assembly, apparatus and process that affords uniformity in all units of a lyophilization batch.

Embodiments of the present invention that meet one or more the foregoing objectives are summarized below. However, this simplified summary of one or more embodiments of the present invention is intended to provide a basic understanding of such embodiments and thus is not meant to be an extensive overview of all contemplated embodiments. Nor is the following summary intended to identify key or critical elements of all embodiments nor to delineate the scope of any or all embodiments. Rather, its sole purpose is to present some concepts of one or more embodiments in a simplified form as a prelude to the more detailed description that is presented later.

In a first aspect, the present invention provides a lyophilization assembly, apparatus and method having optimized lyophilization cycle timelines and thereby shortened into more favorable timelines, wherein the lyophilization assembly includes a thermal block made from heat conductive material, preferably a material having high heat conductivity. In preferred embodiments, the thermal block includes a plurality of identical wells evenly arrayed across multiple rows, wherein the wells are configured to receive containers for lyophilization that contain products to be lyophilized.

In preferred embodiments, the wells are sized and shaped to closely approximate the dimensions of the corresponding containers, more particularly to cause deformation to a polymeric container placed therein. In this manner, substantial contact is created between the outer walls of each container and the interior walls of its respective well which, in turn, allows heat to be evenly transferred at a faster rate from the block to the containers and finally to the product in the containers.

In certain embodiments, both the wells and the containers are square-shaped, such that the square-shaped containers can closely fit into the square-shaped wells. In other embodiments, both the wells and containers exhibit coordinating rounded profiles. In either case, the containers preferably take the form of a syringe barrel in which the product can be lyophilized directly.

Thus, in view of the above, it is an objective of the present invention to provide a lyophilization syringe suitable for in situ lyophilization of an initial product as well as reconstitution and dispensing of a lyophilized product, wherein the syringe is composed (i) an elongate central barrel having a hollow bore configured to retain the initial product to be lyophilized and optionally provided with a wide radial flange at its proximal end; (ii) an open distal tip configured to engage a hypodermic needle assembly and optionally sealed by a distal stopper, such as luer cap, and (iii) an open proximal end configured to receive and/or include a sealing piston and dispensing plunger, wherein said central barrel has a polygonal cross-section, preferably a substantially square cross-section characterized by four elongate side panels that optionally bow outward to form a convex exterior surface. The lyophilization syringe may optionally further include a venting cap removably mounted to the open proximal end, whereby when said cap is partially inserted into the proximal opening, a passage for gaseous outflow from the container interior is formed, thereby providing an escape path for outgassing during the lyophilization process, further wherein the passage is closed when the cap is fully inserted into the proximal opening, such that the lyophilized product is sealed within the container interior.

A further objective of the present invention is to provide a lyophilization apparatus composed of:
a. a thermal block made from a heat conductive material, optionally of metal, preferably of aluminum, characterized by a top side, a bottom side, and a medial thickness extending therebetween, wherein the block is provided with a plurality of uniform wells, each of which is configured to receive a single container, wherein the wells are arranged on said top side and of a predetermined depth, optionally extending through the medial thickness of the block such that each well is comprised of a proximal opening disposed in the top side of said block and a distal exit in the bottom side of the block; and
b. one or more containers, each of which is optionally fabricated from a resilient polymer, preferably polypropylene, wherein each container optionally takes the form of a vial, an ampoule or a dispensing syringe, characterized by deformable lateral walls defining an exterior surface, a hollow interior configured to retain a product in its initial and lyophilized forms, and a proximal opening;
wherein associated wells and containers are analogously sized and shaped, whereby insertion of a container into its respective well causes said lateral walls to deform, thereby directly compressing the exterior surface of the container is against an inner wall of the respective well.

In preferred embodiments, each container takes the form of a dispensing syringe characterized (i) an elongate central barrel having a hollow bore configured to retain the product to be lyophilized, (ii) an open distal tip configured to engage a hypodermic needle assembly, wherein each open distal tip is optionally sealed by a distal stopper and preferably takes the form of a Luer taper configured to receive a distal stopper in the form of a Luer cap, and (iii) a proximal opening is configured to receive a sealing piston and dispensing plunger. In particularly preferred embodiments, the central barrel (a) has a substantially square cross-section characterized by four elongate side panels, wherein each of the side panels optionally bow outward to form a convex exterior surface that compresses against the inner wall of its respective well; and (b) optionally includes a wide radial flange that rests against the proximal opening of its corresponding well so as to prevent vertical displacement of the syringe from the thermal block.

It is yet another objective of the present invention to provide a lyophilization assembly comprised of the above lyophilization apparatus, optionally including the above lyophilization syringe, in which one or more containers are each inserted into a respective well, in combination with a means for alternatively sealing and venting the respective interiors of the one or more containers. In one embodiment, the means for alternatively sealing and venting the respective interiors of the one or more containers takes the form of a series of container caps, each of which is removably mounted to the proximal opening of a corresponding container, whereby when the cap is partially inserted into the proximal opening, a passage for gaseous outflow from the container interior is formed, thereby providing an escape path for outgassing during the lyophilization process, further wherein the passage is closed when the cap is fully inserted into the proximal opening, such that the lyophilized product is sealed within the container interior. Alternatively, the means for alternatively sealing and venting the respective interiors of the one or more containers make take the form of (a) a sealing member configured to cover the top side of the block and the plurality of wells, the sealing member, optionally a silicone pad, having a first venting mechanism, optionally a series of apertures configured to allow vapors to escape from the one or more containers, and (b) a plate, optionally of a rigid material such as metal, glass, or carbon fiber filled polymeric composite, configured to secure the sealing member to the block, the plate having a second venting mechanism, optionally in the form of a series of perforations configured to allow the vapors received through the first mechanism to escape. In preferred embodiments, the plate perforations align with the silicone pad apertures but are offset from the axis of the respective proximal openings so as to prevent fluid leakage.

In a preferred embodiment, the lyophilization assembly further includes an ejector plate to assist in the removal of the one or more containers from the thermal block, the ejector plate being composed of a planar base having a plurality of vertical portions protruding therefrom, wherein the vertical portions are identical in number and spatial orientation to that of the plurality of wells such that moving the block-container apparatus downward onto the vertical portions causes the containers to be dislodged from their respective wells.

Finally, it is yet a further objective to provide a method for lyophilization that utilized the aforementioned lyophilization assembly to lyophilize a product in situ, wherein the method includes the steps of:

a. placing one or more containers in an upright position into the plurality of wells, wherein the proximal openings face up;
b. via the respective proximal openings, filling each container with a product to be lyophilized;
c. engaging the means for sealing and venting the respective interiors of the one or more containers so as to allow vapors to escape from the one or more containers while preventing product from leaking;
d. optionally rotating the lyophilization assembly from the vertical configuration, wherein the proximal openings face up, to the horizontal, wherein proximal openings face sideways, so as to enhance the efficiency of the lyophilization process; and
e. applying heat to the thermal block until all water is removed from the product to be lyophilized.

These and other objectives and features of the invention will become more fully apparent when the following detailed description is read in conjunction with the accompanying figures and examples. However, it is to be understood that both the foregoing summary of the invention and the following detailed description are of a preferred embodiment, and not restrictive of the invention or other alternate embodiments of the invention. In particular, while the invention is described herein with reference to a number of specific embodiments, it will be appreciated that the description is illustrative of the invention and is not constructed as limiting of the invention. Indeed, various modifications and applications will readily occur to those who are skilled in the art, without departing from the spirit and the scope of the invention, as described by the appended claims. In addition, those skilled in the art will recognize that one or more aspects of this invention can meet certain objectives, while one or more other aspects can meet certain other objectives. Moreover, each objective may not apply equally, in all its respects, to every aspect of this invention. As such, the preceding objectives and subsequently presented preferred embodiments can be viewed in the alternative with respect to any one aspect of this invention.

V. BRIEF DESCRIPTION OF THE FIGURES

Various aspects and applications of the present invention will become apparent to the skilled artisan upon consideration of the brief description of figures and the detailed description of the present invention and its preferred embodiments that follows:

FIG. 13 is a perspective view of a distal stopper for a syringe barrel of the present invention.

FIG. 14 is a side elevational view of the objects of FIG. 13.

FIG. 15 is an axial view of the objects of FIG. 13.

FIG. 54 is a side elevational view of the objects of FIG. 52.

FIG. 55 is a sectional view of the objects of FIG. 54 at location A-A.

FIG. 73 depicts an eight step in which the sealed syringe is partially ejected from the thermal block segment.

FIG. 74 is a sectional view of the objects of FIG. 73 at location A-A.

VI. DETAILED DESCRIPTION OF THE PREFERRED EMBODIMENTS

Figure 1:
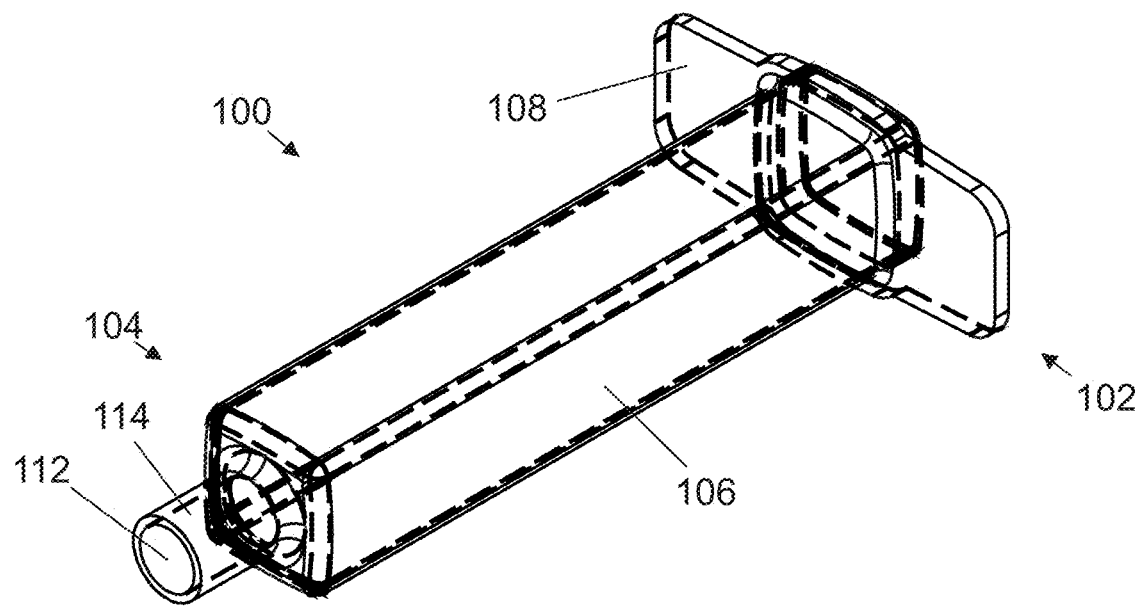
FIG. 1 is a distal perspective view of a syringe barrel formed in accordance with the principles of the present invention.
Figure 2:
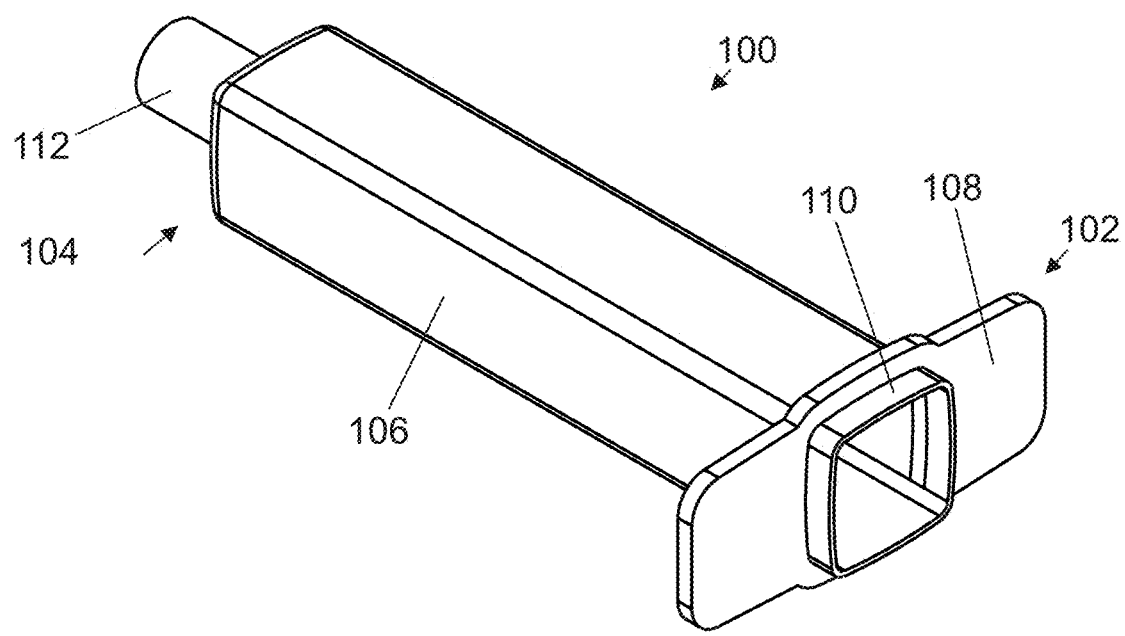
FIG. 2 is a proximal perspective view of the objects of FIG. 1.
Figure 3:
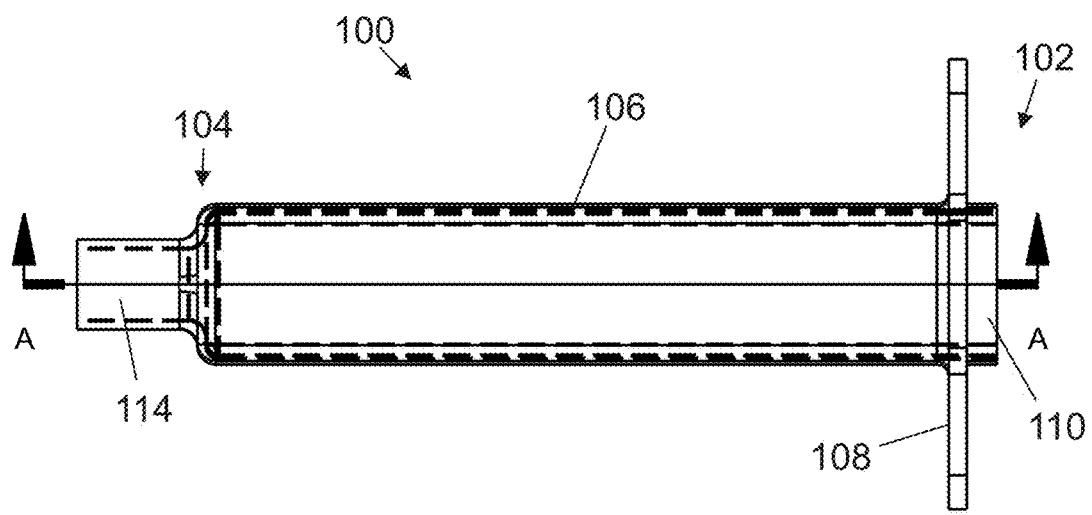
FIG. 3 is a plan view of the objects of FIG. 1.
Figure 4:
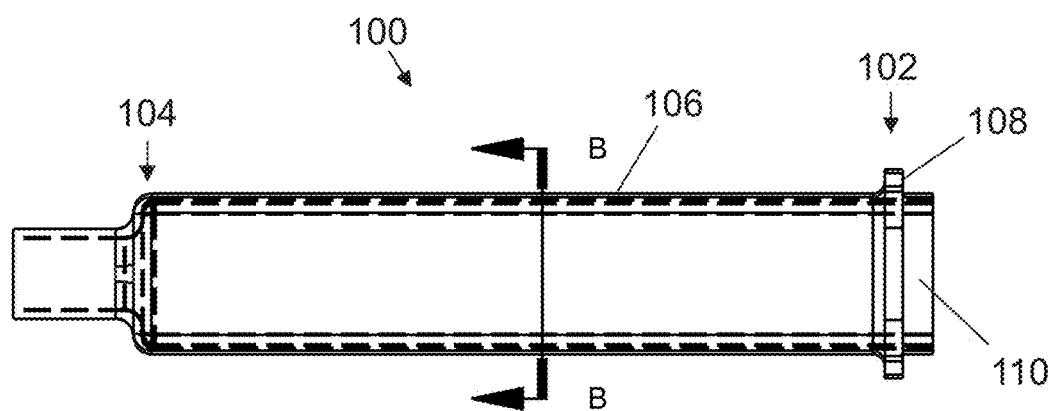
FIG. 4 is a side elevational view of the objects of FIG. 1.
Figure 5:
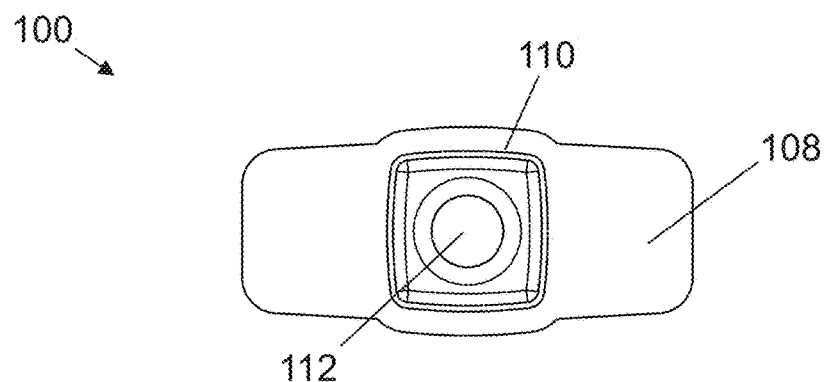
FIG. 5 is a proximal end view of the objects of FIG. 1.
Figure 6:
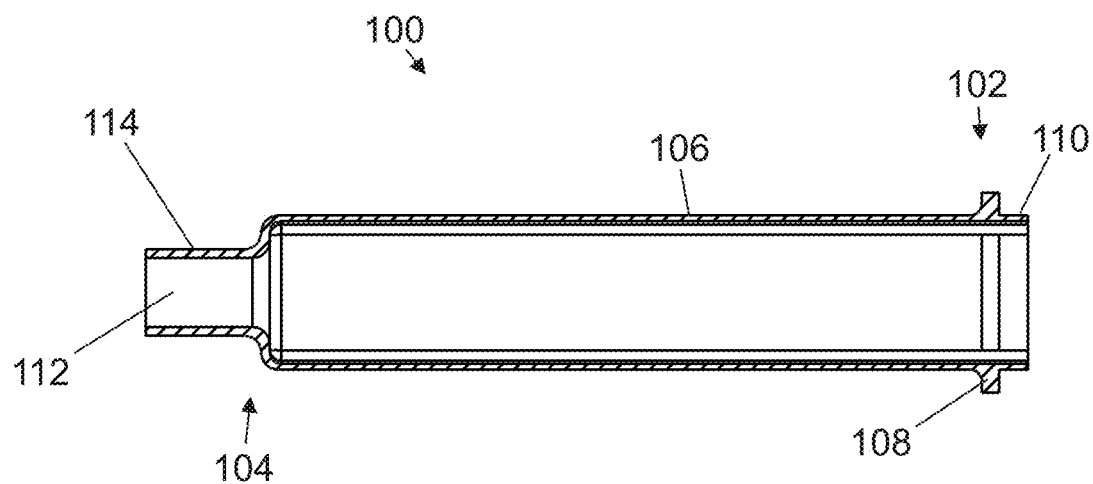
FIG. 6 is a sectional view of the objects of FIG. 3 at location A-A.

While various embodiments are henceforth described, the following description is intended to be exemplary, rather than limiting, and it will be apparent to those of ordinary skill in the art that many more embodiments and implementations are possible that are within the scope of the embodiments. Likewise, although many possible combinations of features are shown in the accompanying figures and discussed in this detailed description hereinbelow, many other combinations of the disclosed features are possible. As such, any feature or element of any embodiment may be used in combination with or substituted for any other feature or element in any other embodiment unless specifically restricted.

Although methods and materials similar or equivalent to those described herein can be used in the practice or testing of embodiments of the present invention, the preferred methods and materials are now described. However, it is to be understood that this invention is not limited to the particular sizes, shapes, dimensions, materials, methodologies, protocols, etc. described herein, as these may vary in accordance with routine experimentation and optimization. It is also to be understood that the terminology used in the description is for the purpose of describing the particular versions or embodiments only, and is not intended to limit the scope of the present invention which will be limited only by the appended claims. Accordingly, unless otherwise defined, all technical and scientific terms used herein have the same meaning as commonly understood by one of ordinary skill in the art to which the present invention belongs. However, in case of conflict, the present specification, including definitions below, will control. Thus, in the context of the present invention:

The words "a", "an", and "the" as used herein mean "at least one" unless otherwise specifically indicated. Thus, for example, reference to an "opening" is a reference to one or more openings and equivalents thereof known to those skilled in the art, and so forth.

The term "proximal" as used herein refers to that end or portion of a device that is situated closest to the user of the device, farthest away from the active or operative end of a device. In the context of the present invention, the proximal end of a syringe of the present invention includes the sealing cap, plunger and finger grip portions.

The term "distal" as used herein refers to that end or portion of a device that is situated farthest away from the user of the device, closest to the operative end. In the context of the present invention, the distal end of a syringe of the present invention refers the output end adapted to receive a needle and/or stopper element.

The terms "lengthwise" and "axial" are used interchangeably herein to refer to the direction relating to or parallel with the longitudinal axis of a device.

The term "transverse" as used herein refers to the direction lying or extending across or perpendicular to the longitudinal axis of a device.

The term "lateral" pertains to the side and as used herein, refers to motion, movement, or materials that are situated at, proceeding from, or directed to a side of a device.

The term "medial" pertains to the middle, and as used herein, refers to motion, movement or materials that are situated in the middle, in particular situated near the median plane or the midline of the device or subset component thereof.

The terms "tube" and "tubular" are interchangeably used herein to refer to a generally round, long, hollow component having at least one central opening often referred to as a "lumen".

The present invention interchangeably makes reference to "containers" and "product containers" designed to carry an initial product to be lyophilized (generally in liquid form), withstand the temperatures and pressures associated with lyophilization, and store the subsequent lyophilized product until called for use. In the context of the present invention, such containers are preferably fabricated from a deformable polymeric material, such as polypropylene. More particularly, such as in the exemplary embodiments identified above and described in detail below, the product container is preferably the barrel of a syringe. However, it will be readily understood that the container need not be a syringe barrel but rather may take the form of a vial, bottle, ampoule, syringe, tube, or other suitable vessel or receptacle.

In the context of the present invention, the terms "syringe", "syringe body", and "syringe barrel" are used interchangeably to refer to a specialized lyophilized product container, namely dispensing device comprised of a central hollow bore having a distal tip configured to receive a hypodermic needle assembly and an open, often flanged proximal end configured to receive a dispensing plunger/piston. In preferred embodiment, the outside of the barrel is provided with graduated markings indicating the volume of fluid in the syringe.

The distal tip or "needle hub" of a syringe barrel finding utility in the context of the present invention is preferably threaded or tapered so as enable firm connection to a hypodermic needle assembly. Perhaps the most well-known of these is the "Luer taper" or "Luer lock", which simply twists the two together. Alternatively, the needle hub may take the form of a "slip tip", a small, friction-fit connection useful when the syringe is being connected to something not featuring a screw lock mechanism. Similar to this is the "catheter tip", which is essentially a slip tip but longer and tapered, making it good for pushing into things where there the plastic taper can form a tight seal.

Lyophilization methods of the present invention offer decreased cycle times, a contributing factor being improved heat transfer to and from the product. An essential element of this method is a thermal block formed of a suitable metallic material. Accordingly, the present invention refers interchangeably to a "block", "thermal block", and "heat block" fabricated from a heat conductive material and having a plurality of identical wells orderly arrayed about its top surface, wherein each of said wells is configured to receive a container carrying product to be lyophilized. In a preferred embodiment, the block is aluminum, chosen for its light weight and excellent thermal conductive properties.

Wells formed in the top surface of the block are designed and dimensioned to receive suitable containers of product to be lyophilized, such as a vial or a syringe barrel. In the context of the present invention, the wells are sized and shaped to closely accommodate the particular container of choice. For example, in the exemplary embodiments described in detail below, the containers take the form of syringe barrels having a substantially square cross-section, wherein sides are optionally bowed outward to form convex outer surfaces. The associated wells are analogously shaped and configured to cause deformation of the syringe barrel in a manner that causes the outer walls of the barrel to be compressed against the inner walls of the well so as to create close contact and optimal conditions for heat conduction. However, one of skill in the art will recognize that the principles taught herein are applicable to syringe barrel shapes other than substantially square. For instance, the shape may be rectangular, a regular or irregular polygon, oval or oblong, circular, or may have an irregular curvilinear profile. So long as the shape allows deformation when inserted into a suitably configured well so as to create substantial intimate contact between surfaces of the barrel and of the well, it falls within the scope of this invention.

In the methods of the present invention exemplified below, a plurality of resilient polymeric syringe barrels, each of which having a substantially square cross-section, are singularly introduced into a corresponding plurality of wells evenly arrayed about the top surface of a metallic thermal block, wherein the wells are dimensioned in such a way as to cause deformation of the syringe barrel and thereby create intimate contact between outer surfaces of the syringe barrel and well sidewalls. Again, one of skill in the art will recognize that the criticality lies less with the precise shape of the respective containers and wells than with the close contact generated by their connection. Thus, regardless of shape, any lyophilization method in which a polymeric syringe barrel with a first cross-sectional shape is inserted into a well in a metallic block or plate with the well having a second different shape that serves to create surface contact that enhances thermal conductivity therethrough falls within the scope of this invention.

In the embodiments previously herein described and exemplified below, the product container is the barrel of a syringe. It will be understood that the container need not be a syringe but may be a vial or any other suitable container formed of a suitable resilient polymeric material such that, when the container is inserted into the thermal block, the walls of the container deform so as to create intimate contact between outer surfaces of the container and the well into which it is inserted. Any such product container falls within the scope of the present invention.

In the context of the present invention, the terms "sealing member", "sealing cap", and "venting cap" are used interchangeably to refer to the cap element designed to coordinate with the open proximal end of the syringe barrel. When positioned in a first configuration in which the cap is partially inserted into the proximal end opening, the cap affords an escape path for outgassing during the lyophilization process. However, when moved into a second configuration in which the cap is fully inserted into the proximal end of the syringe barrel, the cap acts to seal lyophilized product within the syringe barrel.

In the context of the present invention, the terms "subject" and "patient" are used interchangeably herein to refer to any animal (e.g., a mammal), including, but not limited to, humans, non-human primates, canines, felines, rodents, and the like, which is to be the recipient of a particular treatment. In preferred embodiments, the subject is a human, more preferably a patient in need of subcutaneous, intravenous and/or intramuscular pharmaceutical therapy.

Hereinafter, the present invention is described in more detail by reference to the Figures and Examples. However, the following materials, methods, figures, and examples only illustrate aspects of the invention and are in no way intended to limit the scope of the present invention. As such, methods and materials similar or equivalent to those described herein can be used in the practice or testing of the present invention.

EXAMPLES

Figure 7:
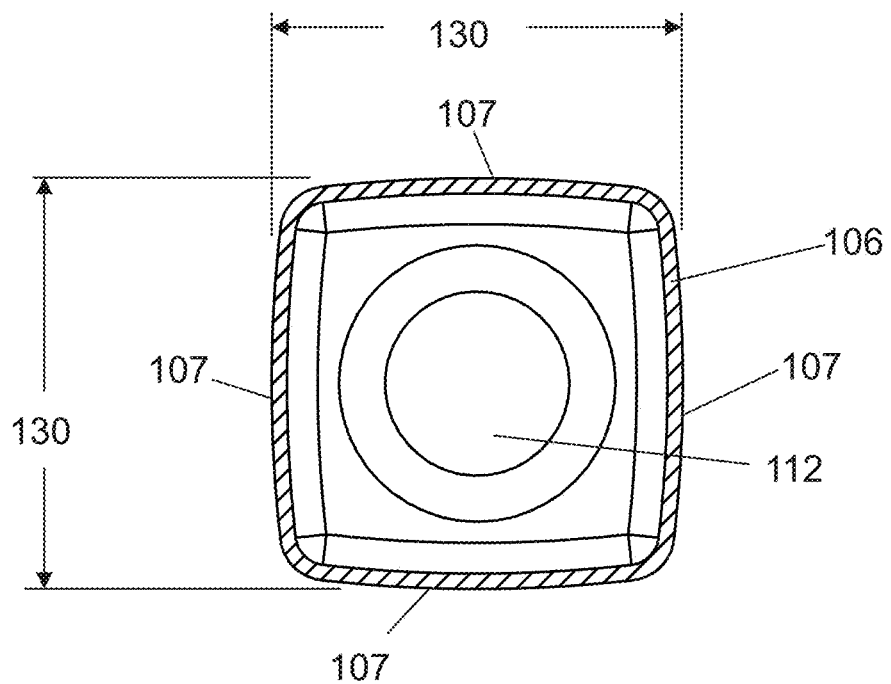
FIG. 7 is an expanded sectional view of the objects of FIG. 4 at location B-B.
Figure 8:
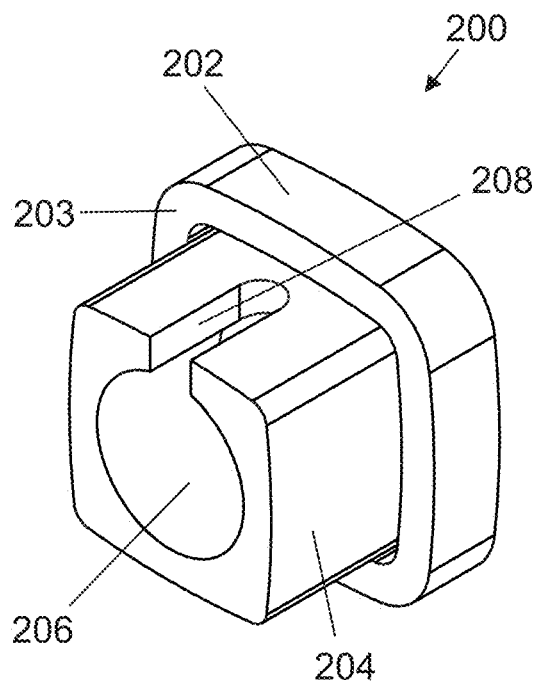
FIG. 8 is a perspective view of a cap for a syringe barrel formed in accordance with the principles of the present invention.
Figure 9:
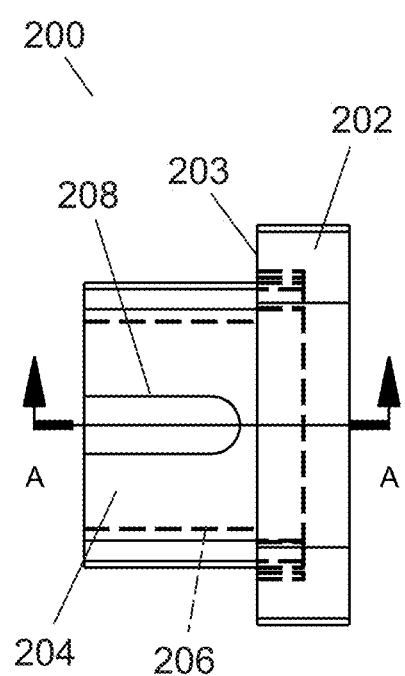
FIG. 9 is a plan view of the objects of FIG. 8.
Figure 10:
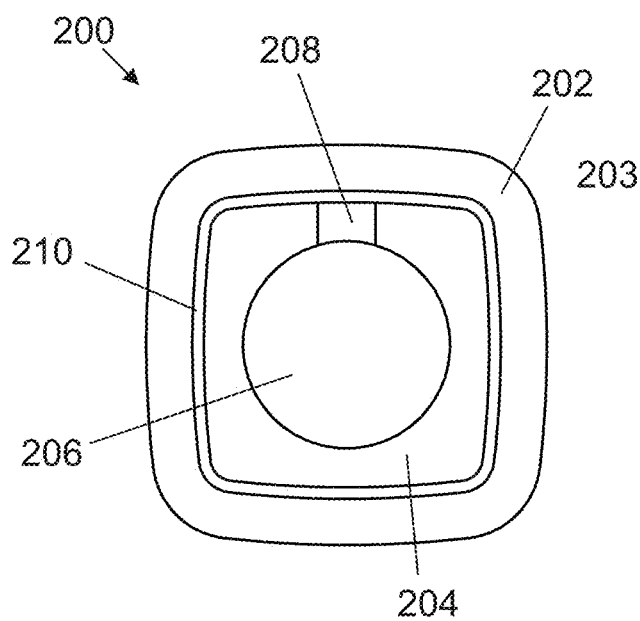
FIG. 10 is a distal axial view of the objects of FIG. 8.
Figure 11:
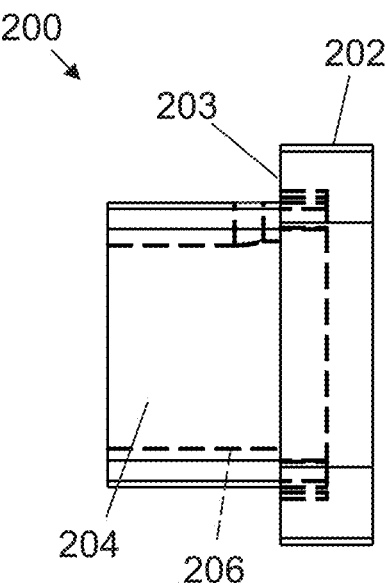
FIG. 11 is a side elevational view of the objects of FIG. 8.
Figure 12:
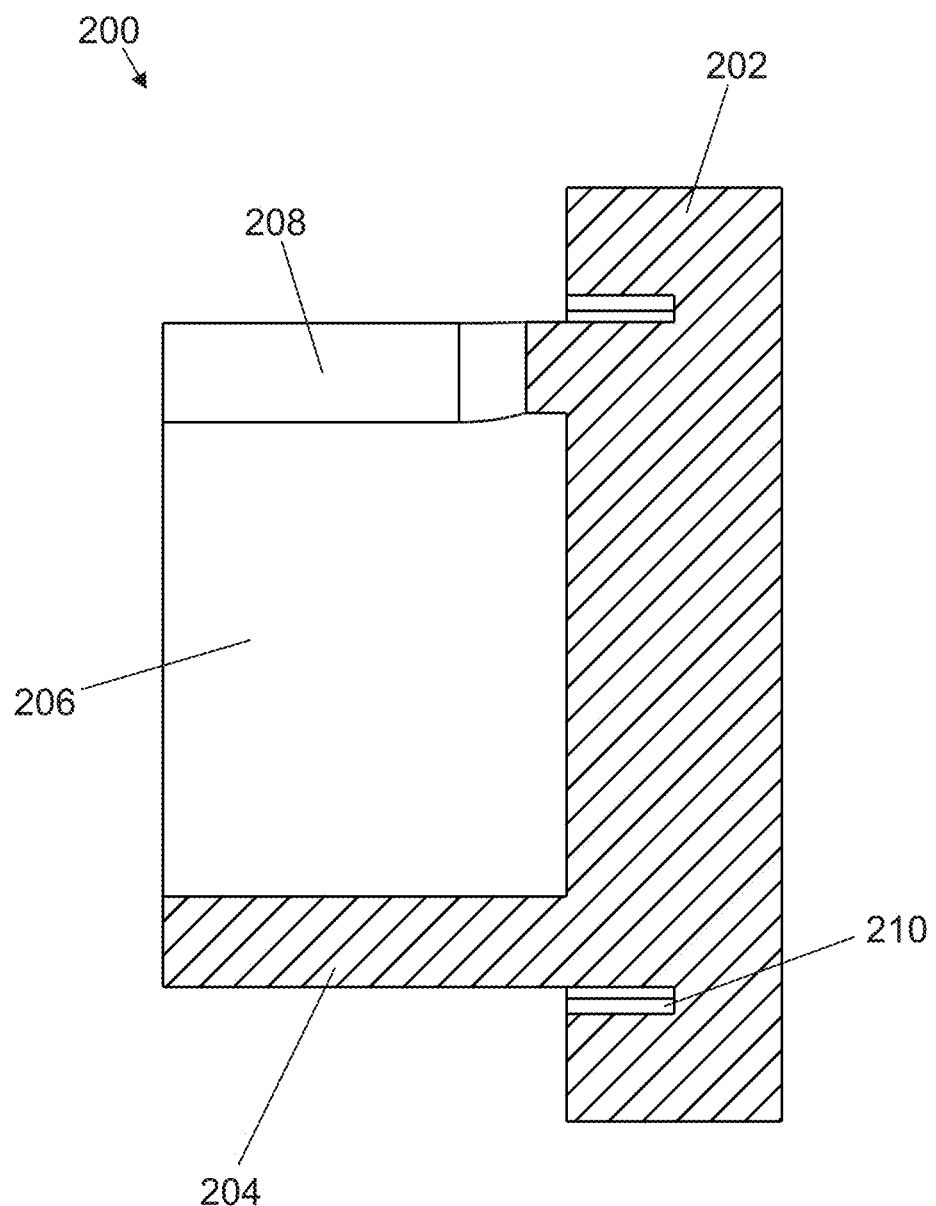
FIG. 12 is an expanded sectional view of the objects of FIG. 9 at location A-A.
Figure 16:
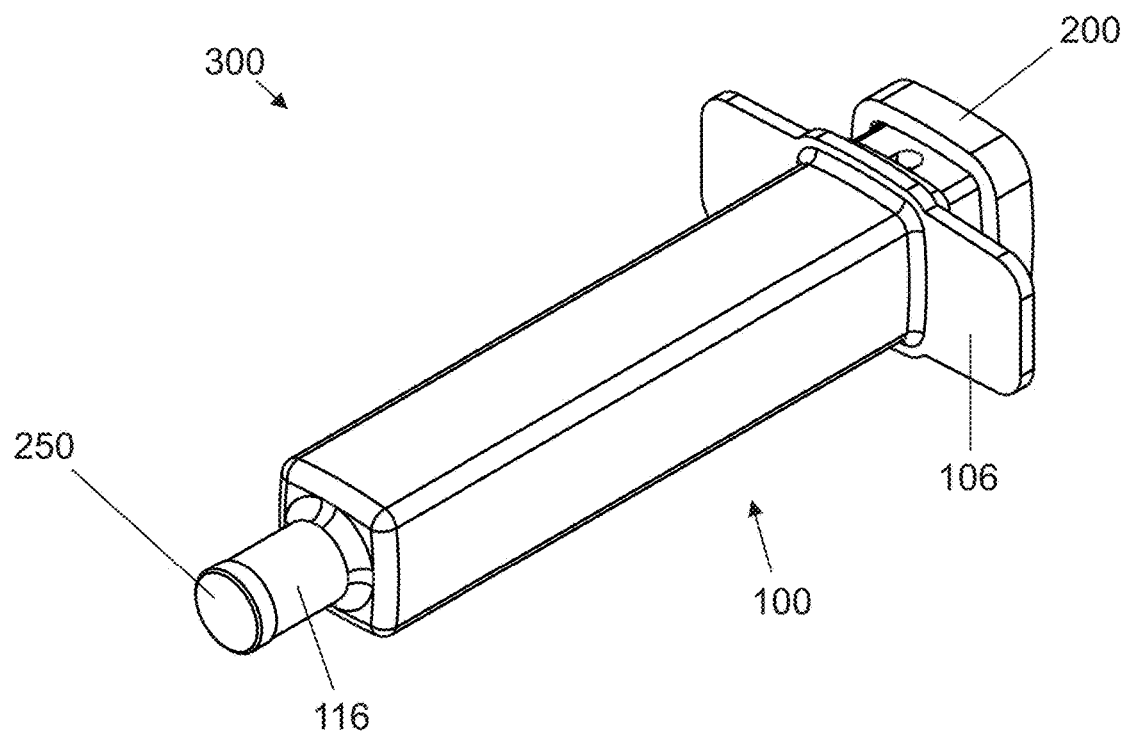
FIG. 16 is a distal perspective view of a syringe barrel assembly of the present in which the cap of FIG. 8 and distal stopper of FIG. 13 are mounted to the syringe barrel of FIG. 1, and wherein the cap is in a first, venting position.
Figure 17:
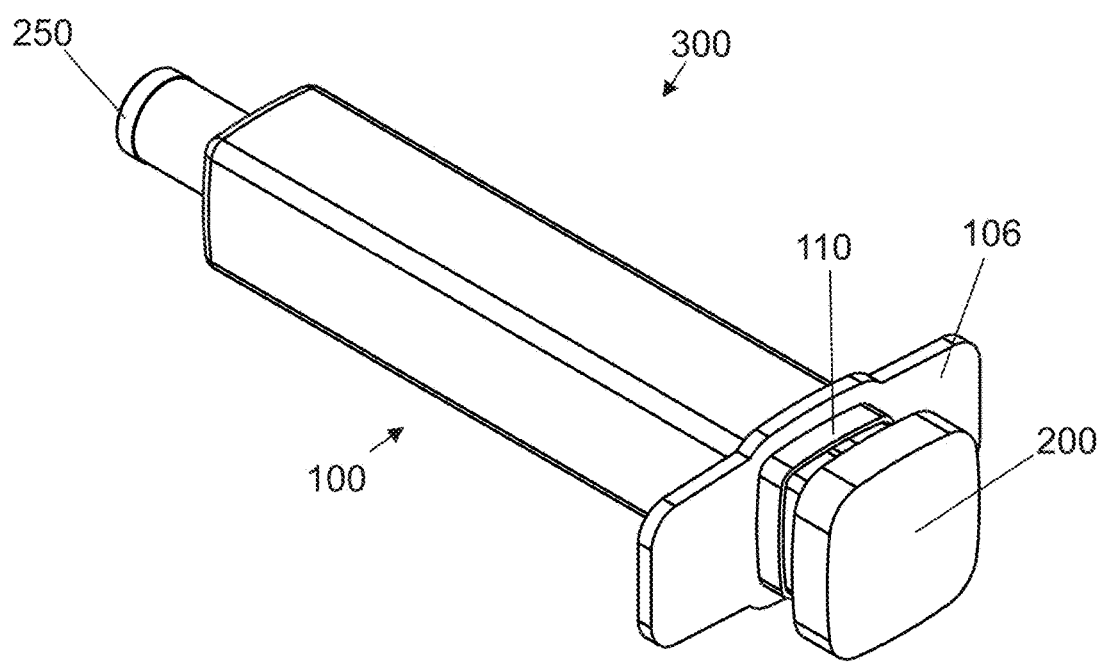
FIG. 17 is a proximal perspective view of the objects of FIG. 16.
Figure 18:
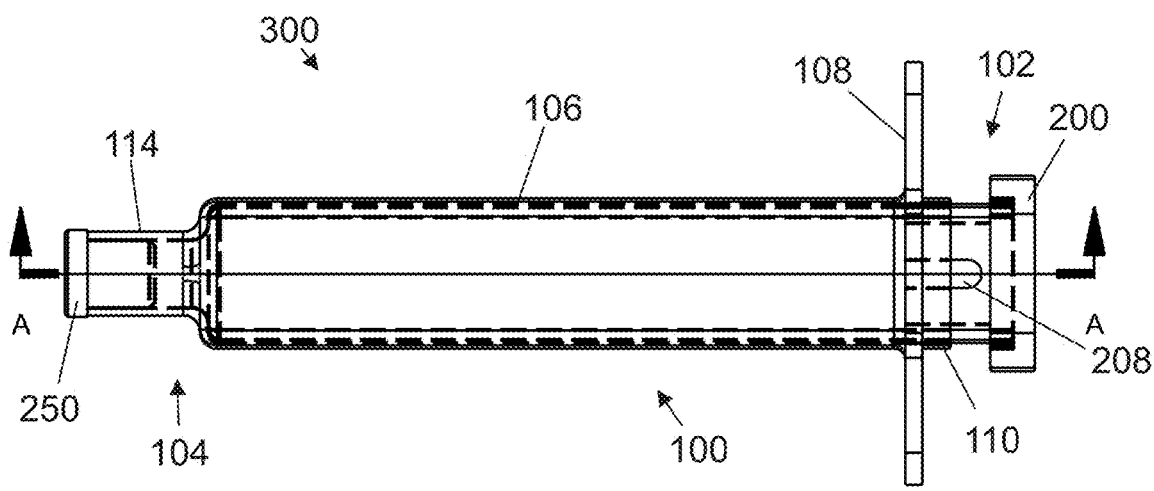
FIG. 18 is a plan view of the objects of FIG. 16.
Figure 19:
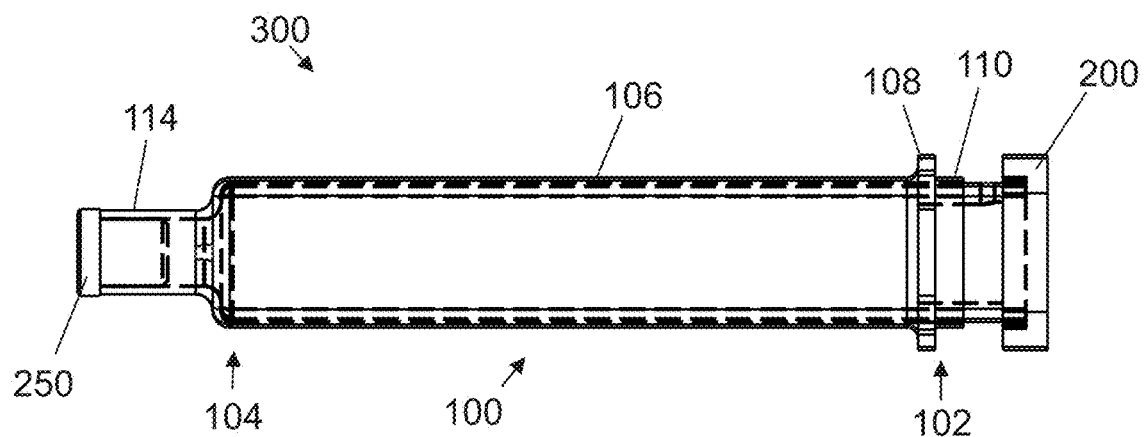
FIG. 19 is a side elevational view of the objects of FIG. 16.
Figure 20:
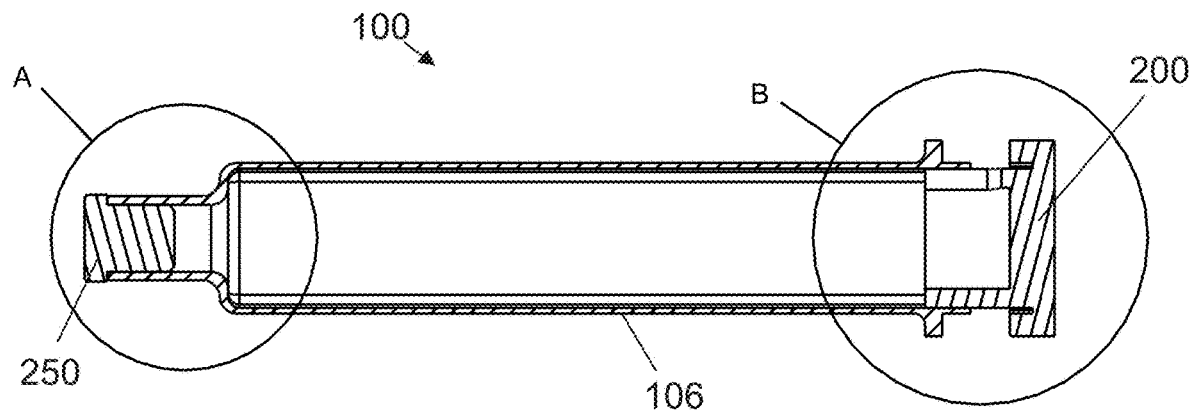
FIG. 20 is a sectional view of the objects of FIG. 18 at location A-A.
Figure 21:
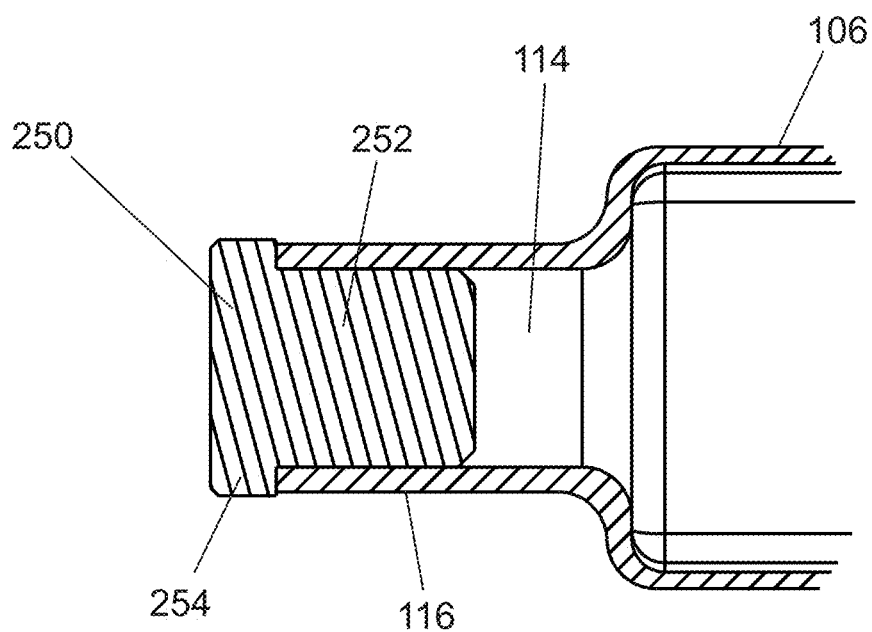
FIG. 21 is an expanded view of the objects of FIG. 20 at location A.
Figure 22:
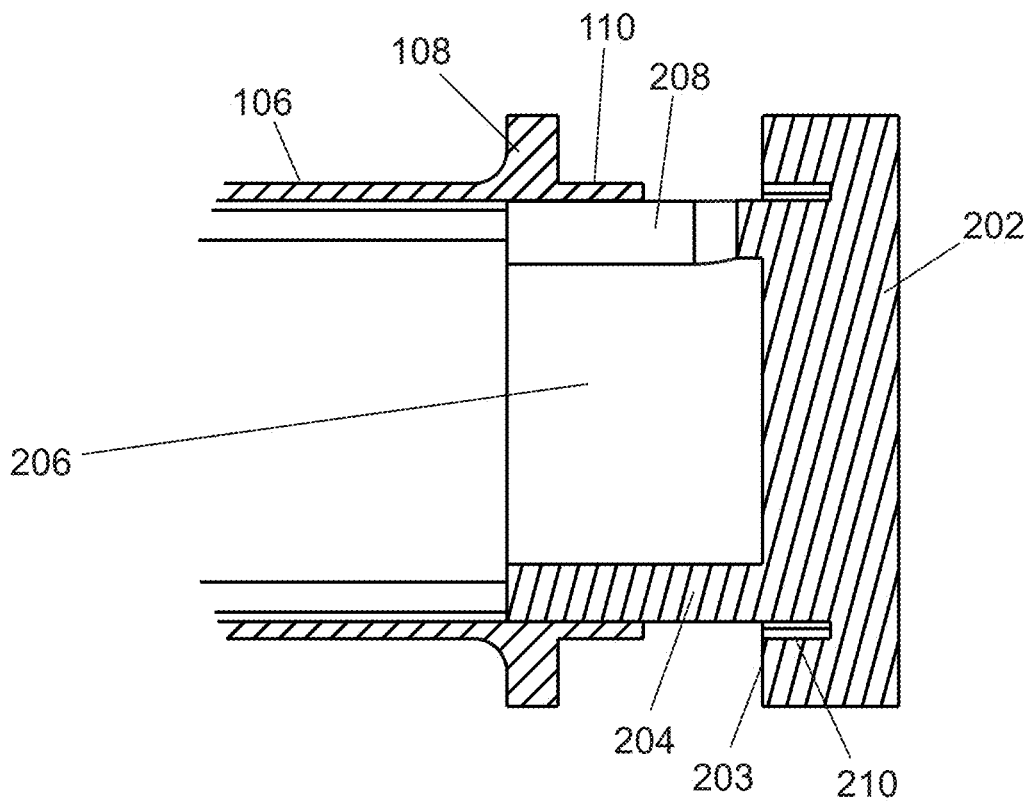
FIG. 22 is an expanded view of the objects of FIG. 20 at location B.
Figure 23:
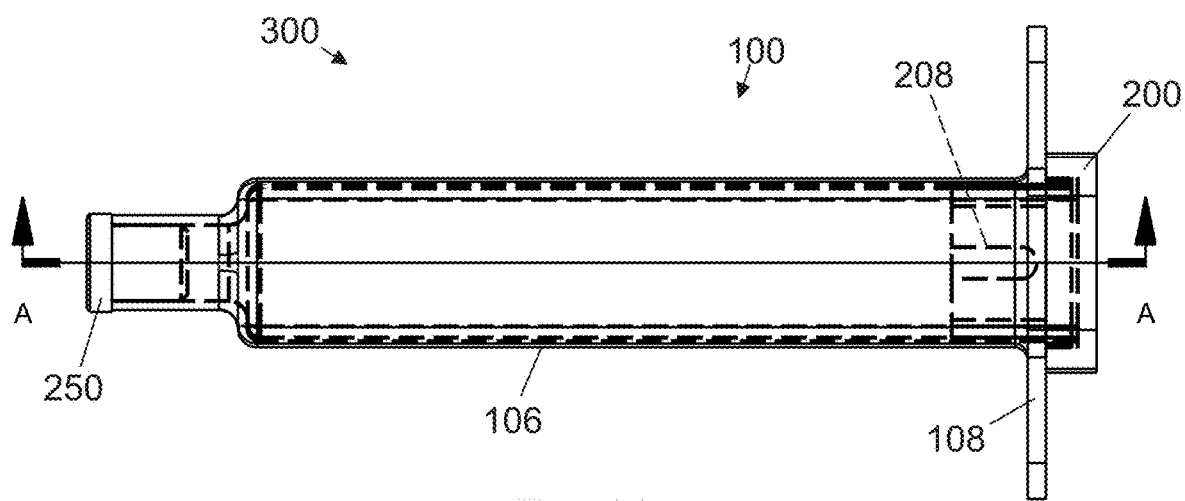
FIG. 23 is a plan view of the objects of FIG. 16 wherein the cap is in a second, sealing position.
Figure 24:
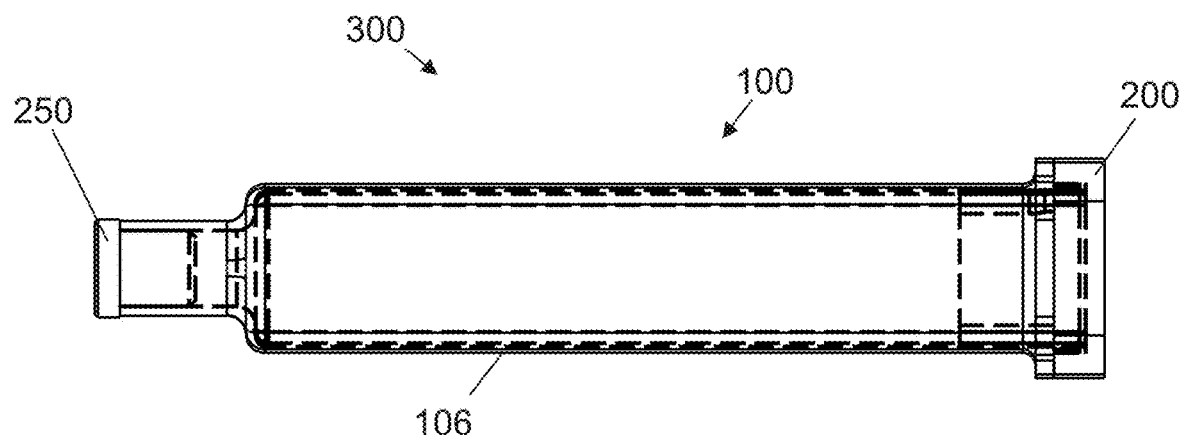
FIG. 24 is a side elevational view of the objects of FIG. 23
Figure 25:
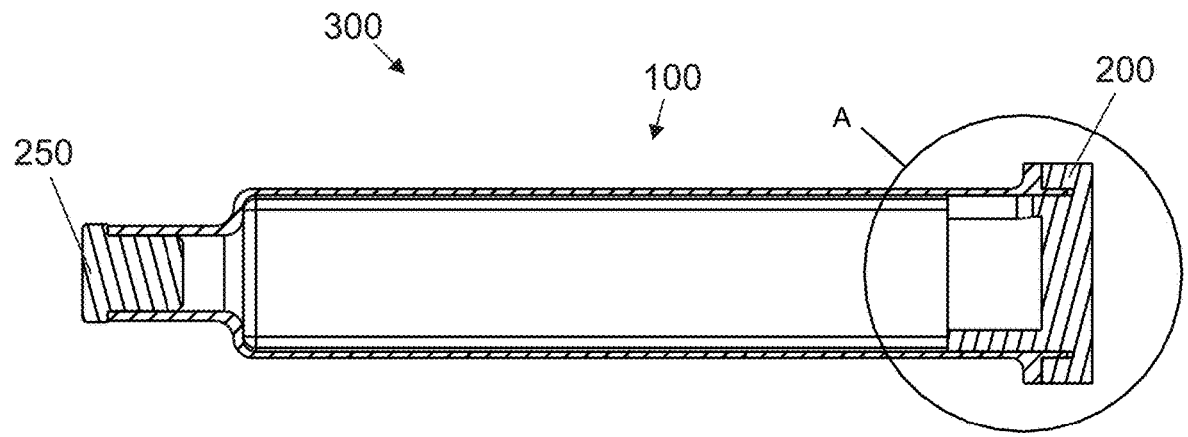
FIG. 25 is a sectional view of the objects of FIG. 23 at location A-A.
Figure 26:
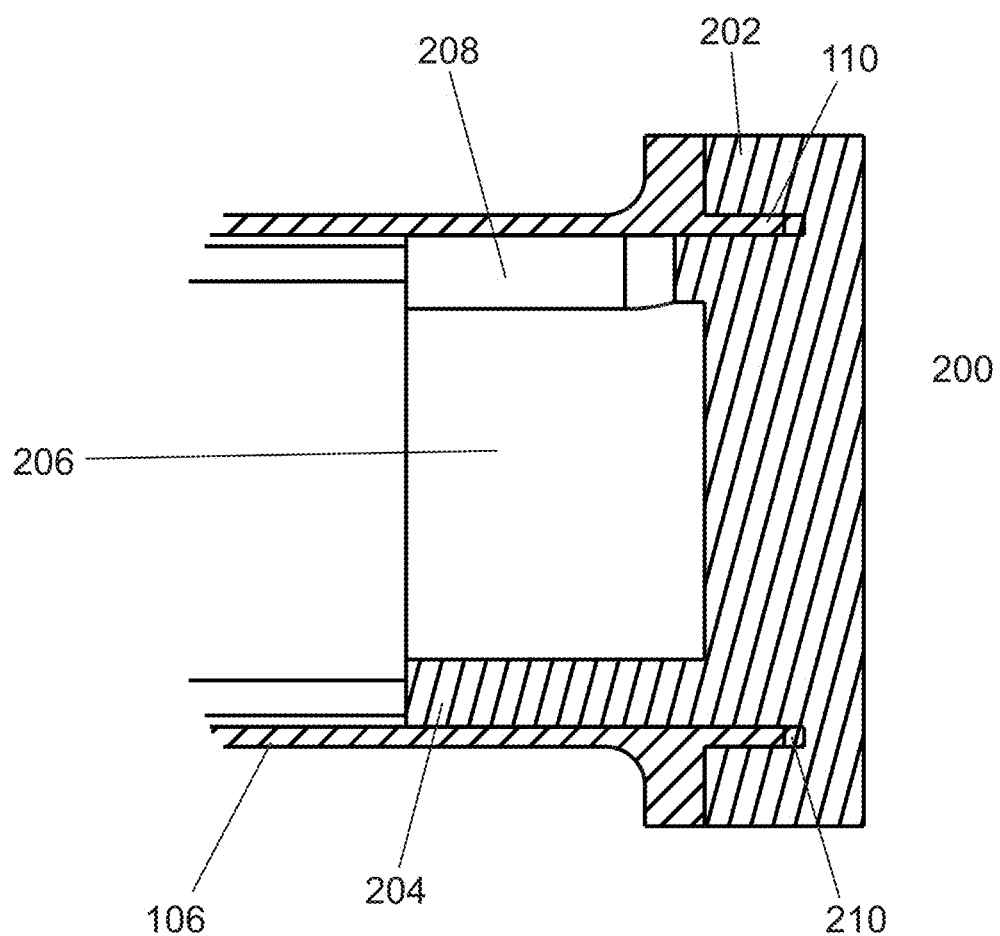
FIG. 26 is an expanded view of the objects of FIG. 25 at location A.

A syringe barrel 100 of the present invention is depicted in FIGS. 1 through 7. Barrel 100 has an elongate mid-portion 106 with barrel flange 108 formed at its proximal end, and distal output portion 112 at its distal end. In preferred embodiments, output portion 112 is a Luer lock or Luer taper. Rim 110 extends proximally from the proximal surface of barrel flange 108. As best seen in FIG. 7, the walls of barrel mid-portion 106 with outer surfaces 107 are not planar, but rather have a predetermined convex shape. Syringe barrel 100 is formed of a resiliently deformable polymeric material. In preferred embodiments, the material is polypropylene.

A cap 200 for removable mounting to the proximal end of syringe barrel 100 is depicted in FIGS. 8 through 12. Cap 200 has a proximal portion 202 and a distal portion 204 wherein is formed distal recess 206 and slot 208. Circumferential groove 210 is formed in the distal surface of proximal portion 202, groove 210 being configured to accept therein rim 110 of syringe barrel 100.

Stopper 250, depicted in FIGS. 13 through 15 is configured for removable placement in output portion 112 of syringe barrel 100. Stopper 250 has a proximal portion 252 and a distal portion 254. In a preferred embodiment, stopper 250 is a Luer cap.

FIGS. 16 through 22 depict syringe assembly 300. Barrel 100 has stopper 250 removably placed in distal output portion 116 of barrel 100 to seal the distal end of barrel 100. Cap 200 is removably mounted to barrel 100 in a first, partially inserted position in which the proximal portion of slot 208 of cap 200 is exposed so as to form a passage for gaseous outflow from the interior of syringe barrel 100.

Syringe assembly as pictured in FIGS. 23 through 26 is identical to assembly 300 of FIGS. 16 through 22 except that cap 200 is fully inserted so that slot 208 is fully covered, thereby isolating the interior of syringe barrel 100 from the surrounding environment.

Hereafter, exemplary methods of the present invention for lyophilization of a product are described.

Figure 27:
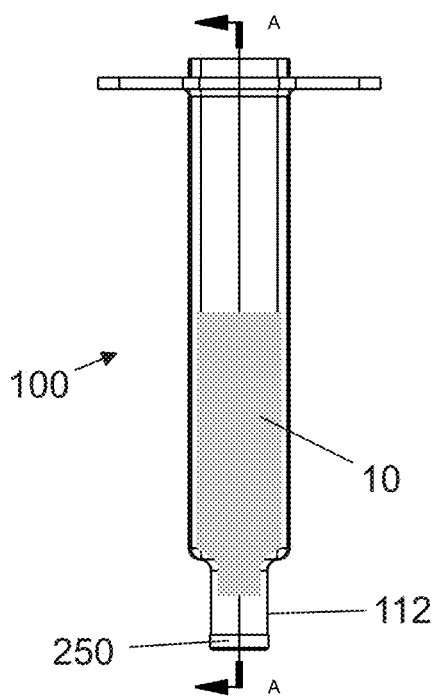
FIG. 27 depicts a syringe barrel of the present invention wherein a fluid to be lyophilized has been placed in a first step of a lyophilization method of the present invention.
Figure 28:
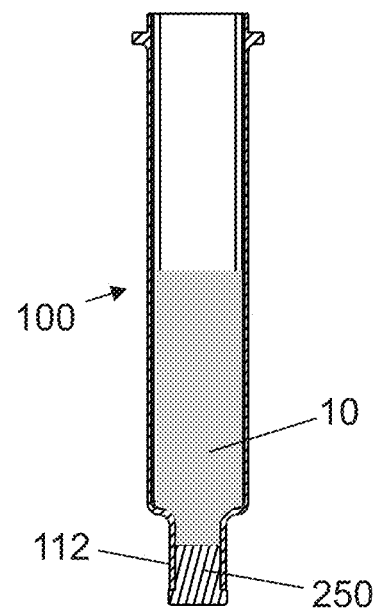
FIG. 28 is a sectional view of the objects of FIG. 27 at location A-A.
Figure 29:
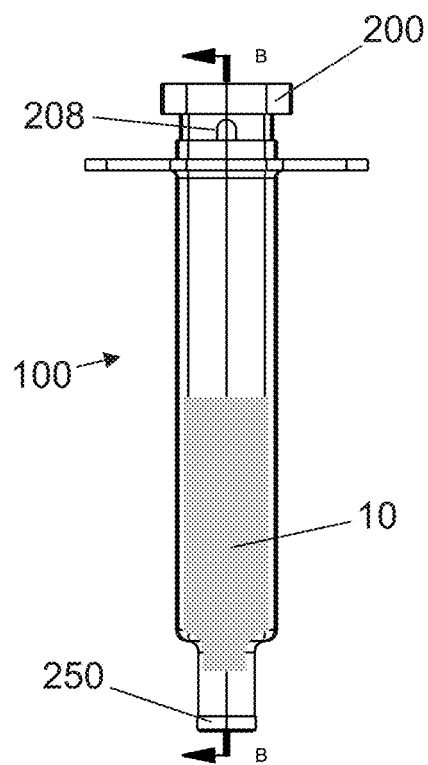
FIG. 29 depicts a second step in the method of the present invention in which the cap is place on the syringe barrel as in FIG. 16.
Figure 30:
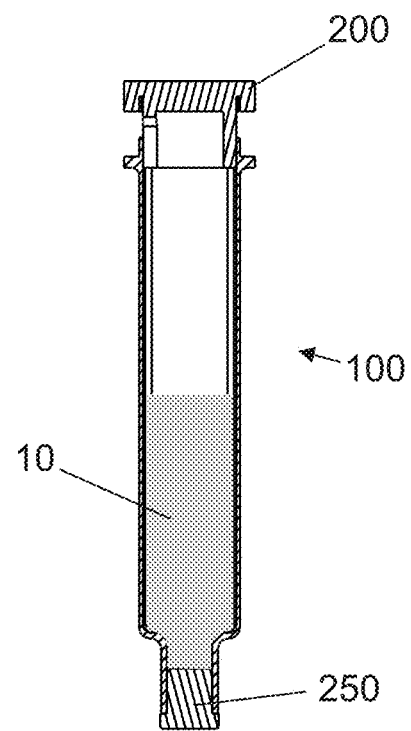
FIG. 30 is a sectional view of the objects of FIG. 29 at location A-A.

In a first step of the method depicted in FIGS. 27 and 28, a product 10 to be lyophilized is placed in syringe barrel 100, with stopper 250 removably inserted in distal portion 112. Referring now to FIGS. 29 and 30, in a second step of the method, cap 200 is inserted into syringe barrel 100 and positioned as depicted in FIGS. 18 through 22, slot 208 in cap 200 being exposed so as to provide an escape path for outgassing during the lyophilization process.

Figure 31:
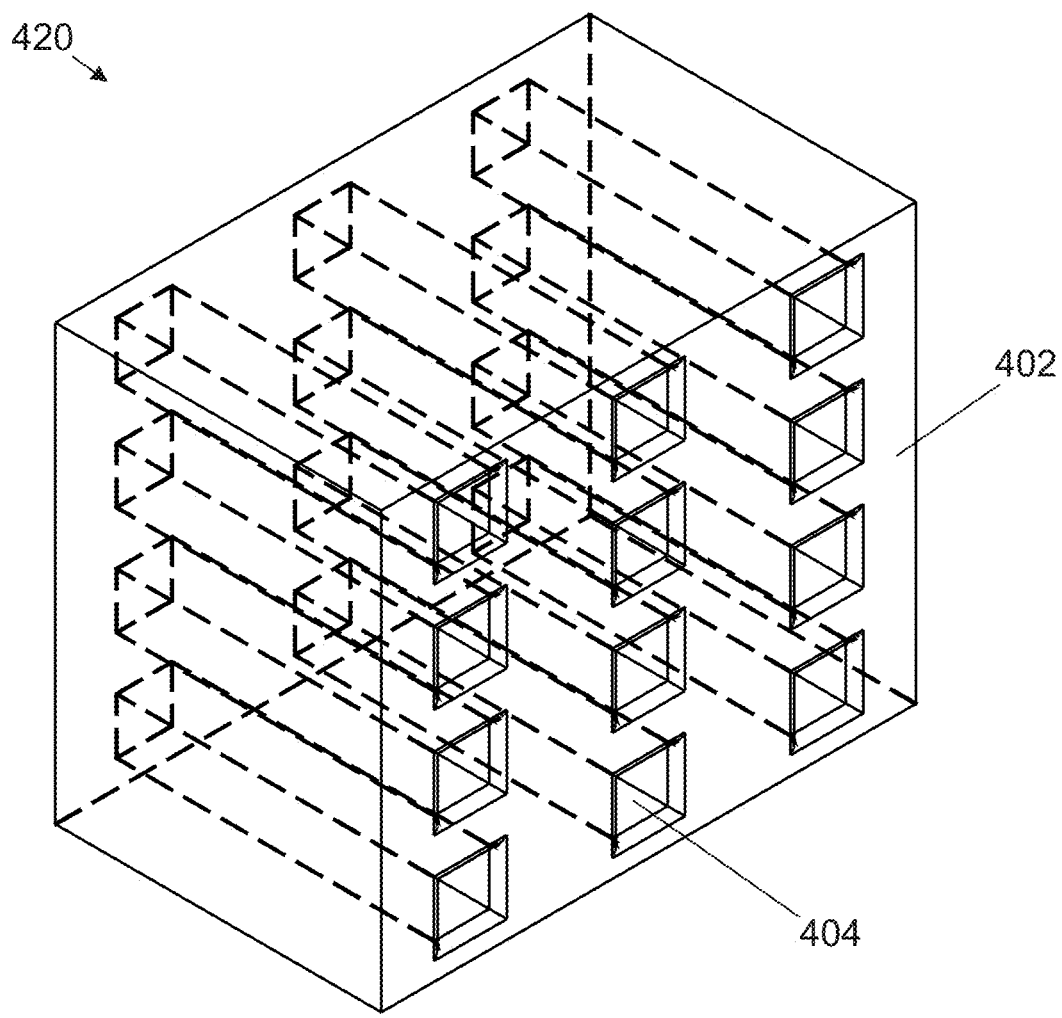
FIG. 31 is a perspective view of a thermal block of the present invention wherein are formed multiple wells for receiving syringe barrels of the present invention.
Figure 32:
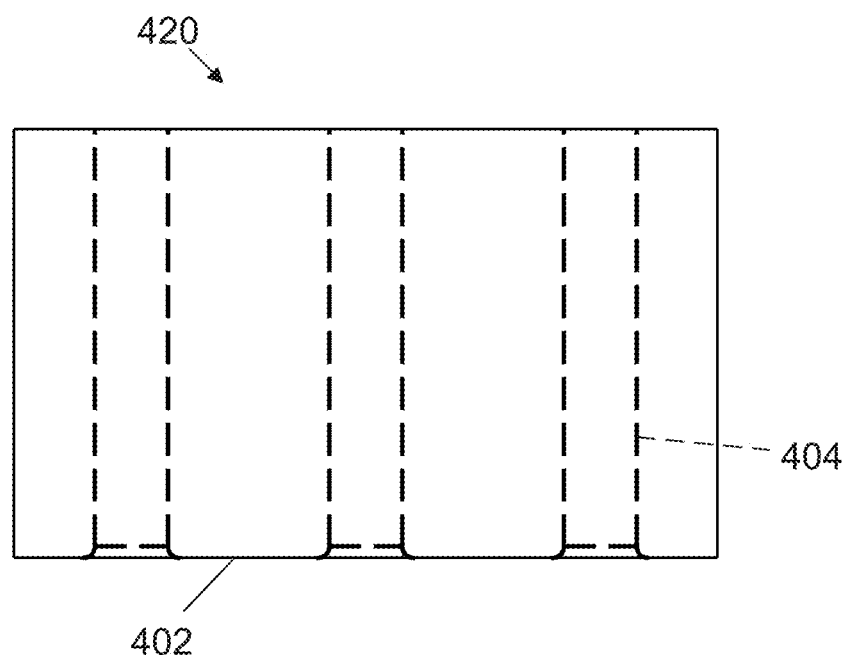
FIG. 32 is a plan view of the objects of FIG. 31.
Figure 33:
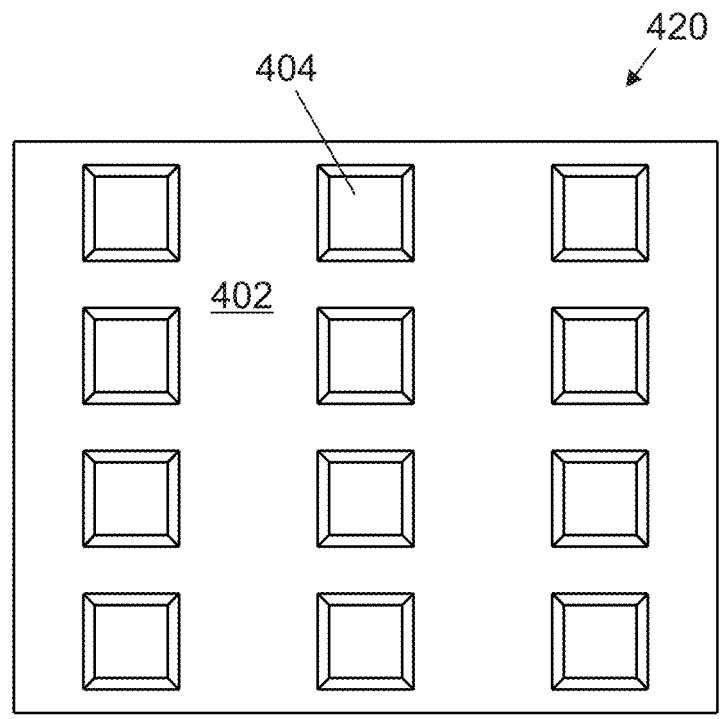
FIG. 33 is an axial end view of the objects of FIG. 31.
Figure 34:
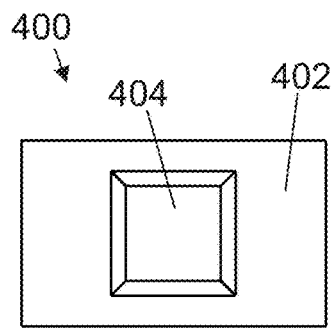
FIG. 34 is a plan view of a segment of the block of FIG. 31 containing a single well, hereinafter used to depict subsequent steps of a lyophilizing method of the present invention.
Figure 36:
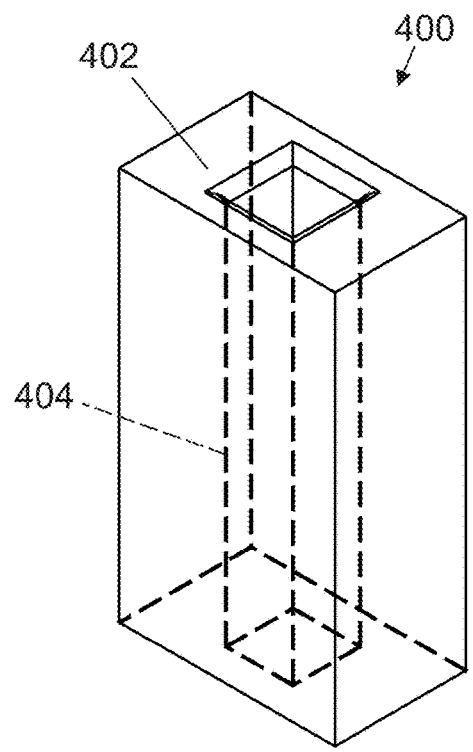
FIG. 36 is a perspective view of the objects of FIG. 34.
Figure 35:
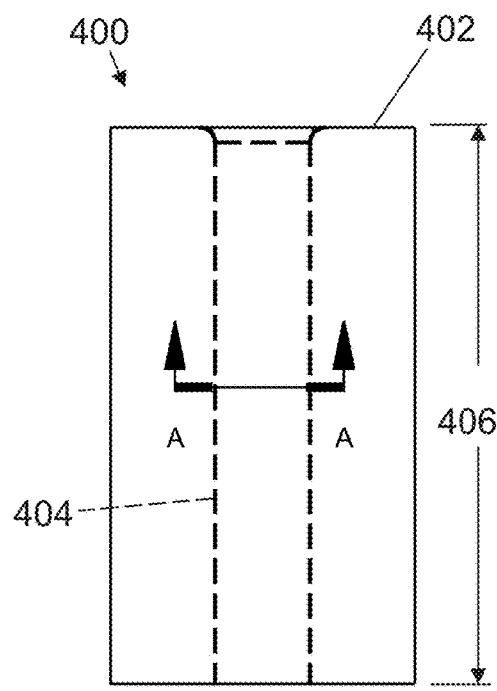
FIG. 35 is a side elevational view of the objects of FIG. 34.
Figure 37:
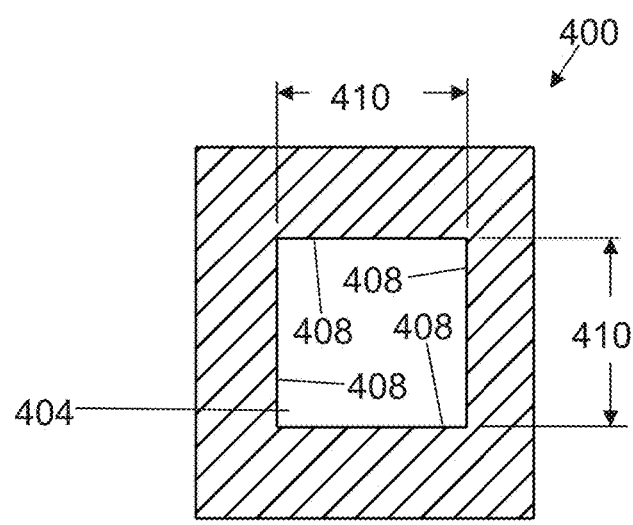
FIG. 37 is an expanded sectional view of the objects of FIG. 35 at location A-A.
Figure 38:
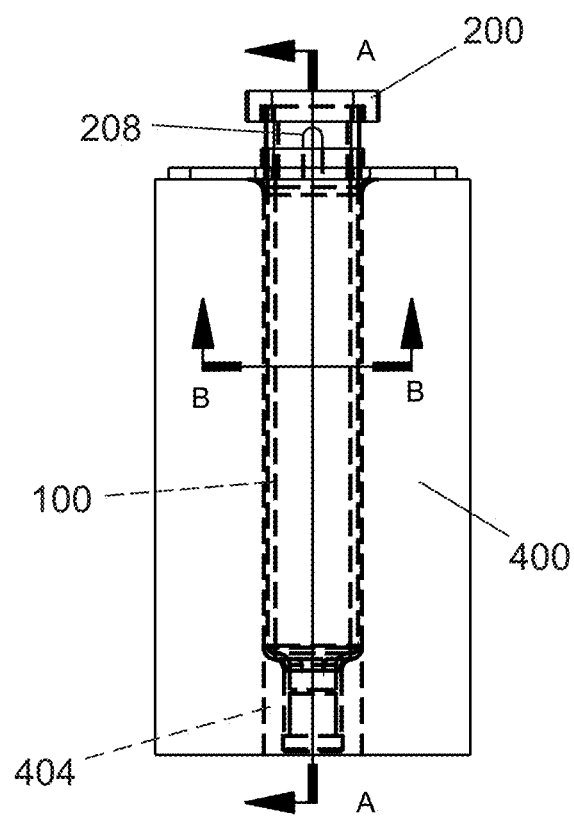
FIG. 38 depicts a third step in lyophilization methods of the present invention in which the syringe barrel with cap is placed in the well of the thermal block of FIG. 31.
Figure 39:
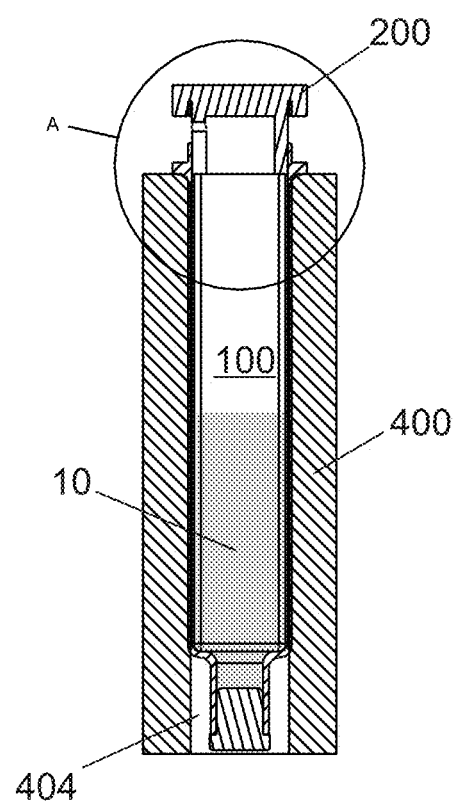
FIG. 39 is a sectional view of the objects of FIG. 38 at location A-A.
Figure 79:
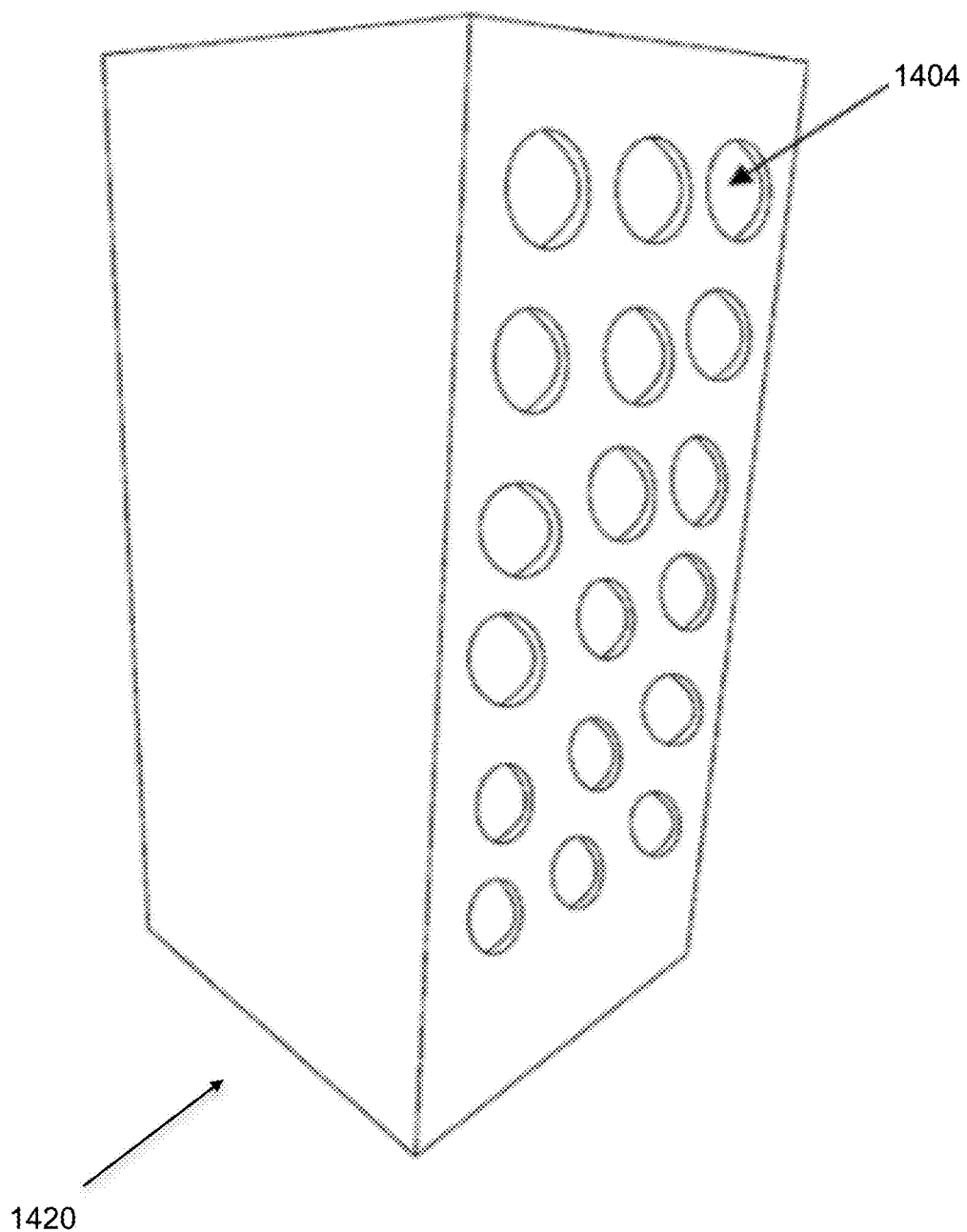
FIG. 79 is a side elevational view of an alternate embodiment of the thermal block of the present invention, wherein are formed multiple rounded wells for receiving syringe barrels of the present invention.

A first embodiment of a block 420 formed in accordance with principles of the present invention is depicted in FIGS. 31 through 33. An alternate embodiment in which the wells 1404 of the inventive block 1420 are more rounded in shape is depicted in FIG. 79. With reference to the former, block 420 has a first surface 402 in which are formed wells 404. The construct and function of block 420 will be now described with regard to a segment 400 of block 420 depicted in FIGS. 34 through 37 wherein segment 400 is oriented so that wells 404 are vertical. Segment 420 has a height 406 and wells 400 have a square shape of width and height 410. Well 404 has side walls 408. For simplicity, hereinafter block segment 400 will be referred to simply as "block" 400. It will be understood that this term refers to a segment of block 420 and is equally applicable to all well-containing segments of block 420.

Figure 40:
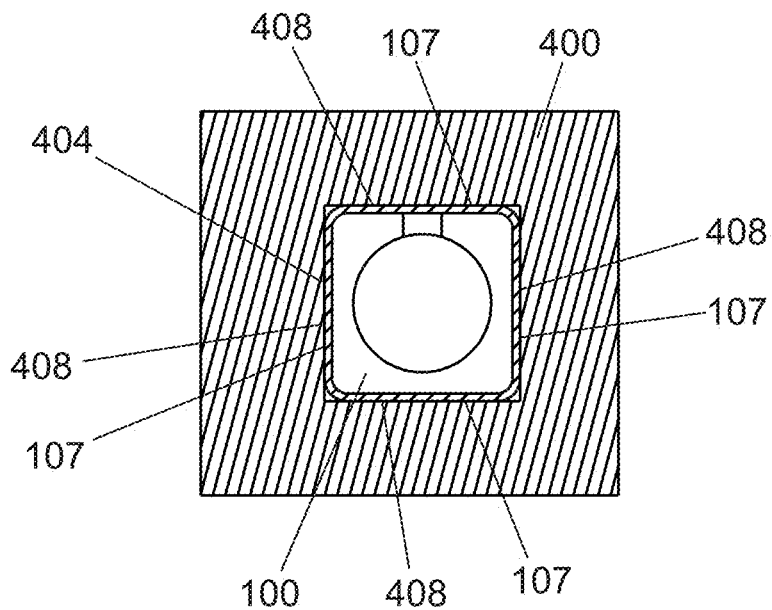
FIG. 40 is an expanded sectional view of the objects of FIG. 38 at location B-B.
Figure 41:
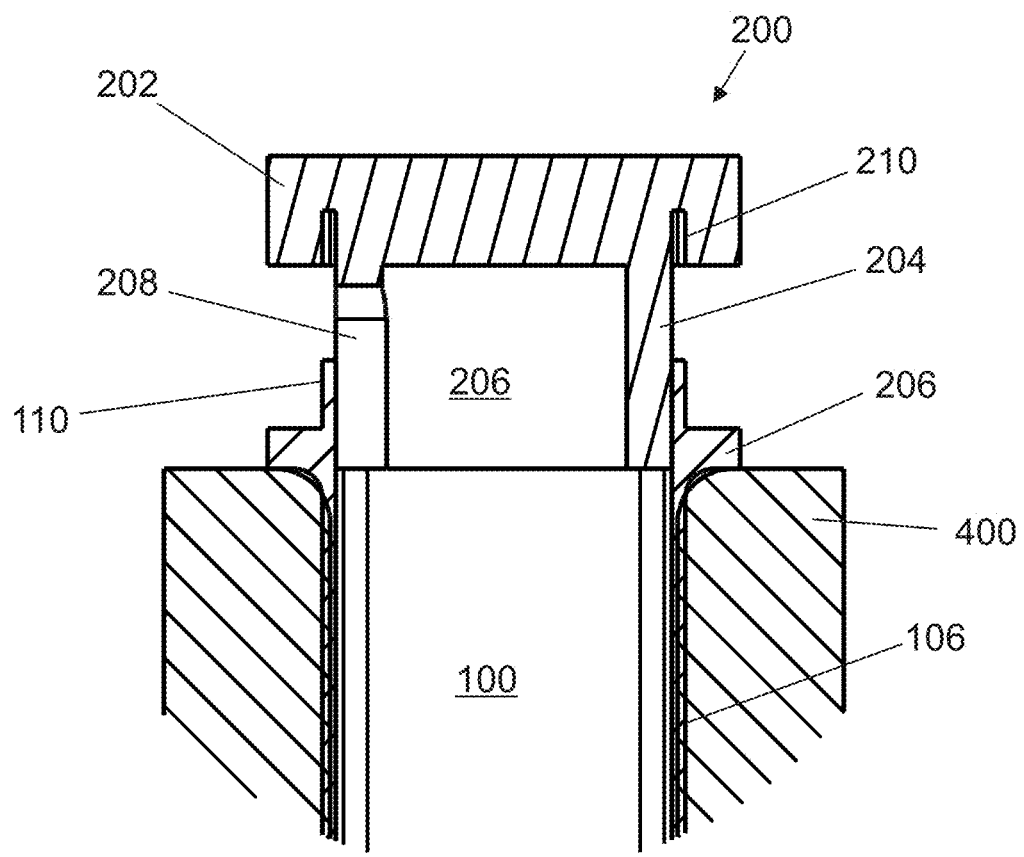
FIG. 41 is an expanded view of the objects of FIG. 39 at location A.

In a third step of a lyophilization method of the present invention, syringe barrel 100 containing product 10 is inserted into block 400 as depicted in FIGS. 38 through 41. As best seen in FIG. 40, mid-portion 106 of syringe barrel 100 is tightly confined within well 404 of block 400, the convex walls of mid-portion 106 (see FIG. 7) being deformed so that outer surfaces 107 of mid-portion 106 of syringe barrel 100 are pressed tightly against inner surfaces 408 of well 404.

As discussed above, a close fit between the vessel containing the product and the well or other shaped cavity in a plate is necessary to achieve conductive heat transfer between the product and the plate. Moreover, it will be understood that conduction can only occur through surfaces that are in contact. If a vessel only closely conforms to the cavity in which it is placed, conduction will occur only in portions wherein the vessel and cavity are in contact. Voids between the vessel and the surrounding cavity effectively insulate the vessel since heat transfer must occur by radiation or convection. In the case of radiation, the temperature difference between the vessel/product and the cavity is insufficient to cause effective cooling. Since the lyophilization process occurs in a vacuum, there is no medium present for convective cooling.

In the assemblies and methods of the present invention, there is intimate contact between outer surfaces 107 of syringe barrel 100 and sidewalls 408 of well 400 so as to allow conductive heat transfer through virtually all walls of mid-portion 106 of syringe barrel 100.

Figure 42:
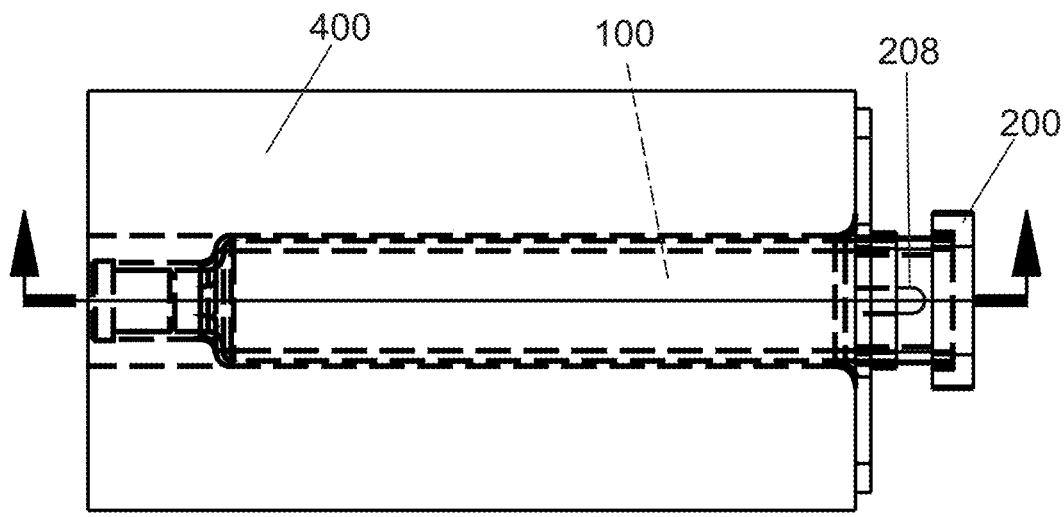
FIG. 42 depicts a fourth step in a lyophilization method of the present invention in which the block and syringe barrel are rotated so that the syringe barrel axis is horizontal and the fluid is in a liquid state.
Figure 43:
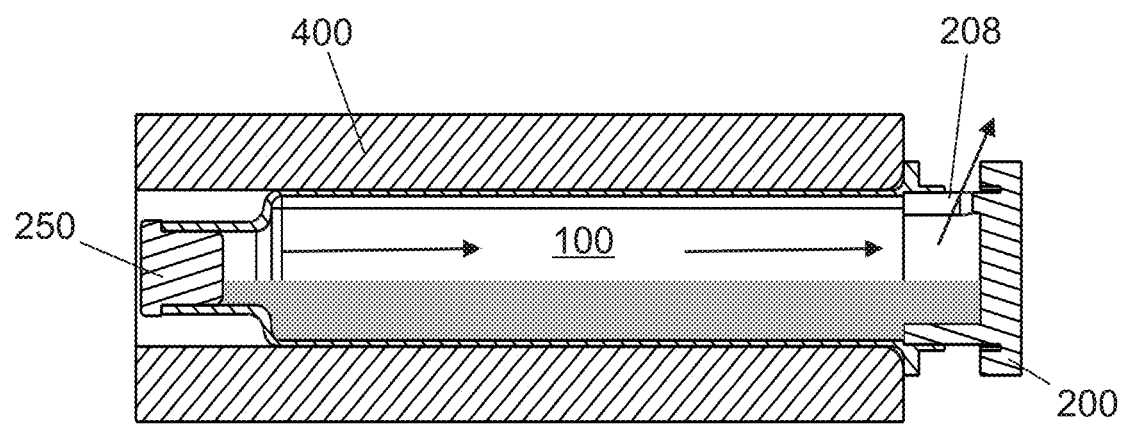
FIG. 43 is a sectional view of the objects of FIG. 42 at location A-A.

In a fourth step in a lyophilization method of the present invention depicted in FIGS. 42 and 43, block 400 and syringe assembly 300 contained therein are reoriented to a horizontal position. During lyophilization, water is removed by sublimation, a process that begins at the free surface of the product and progresses downward until all of the product is sublimated. The time required to complete the process is determined by the vertical distance through which the sublimation process must progress, and the rate of heat transfer to and from product 10. By reorienting block 400 and syringe assembly 300 to the horizontal position, the distance through which sublimation must progress is drastically reduced from what it was with block 400 and syringe assembly 300 in the vertical position. Also, because portions of mid-portion 106 of syringe barrel 100 containing product 10 have wall outer surfaces 107 in contact with inner surfaces 408 of well 404, heat transfer is optimal and evenly distributed to product 10.

Figure 44:
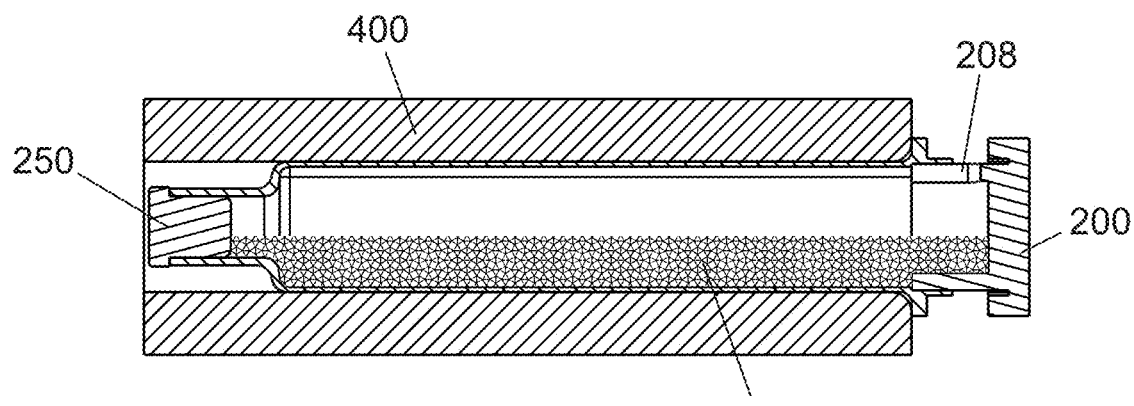
FIG. 44 depicts a fifth step in a lyophilization method of the present invention in which the liquid has been fully lyophilized.
Figure 45:
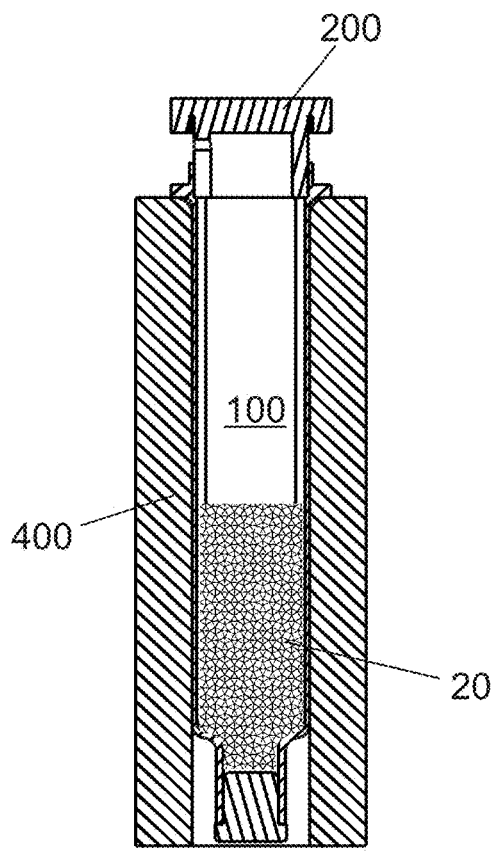
FIG. 45 depicts a sixth step in the method of the present invention wherein the syringe barrel and block are returned to a vertical position.
Figure 46:
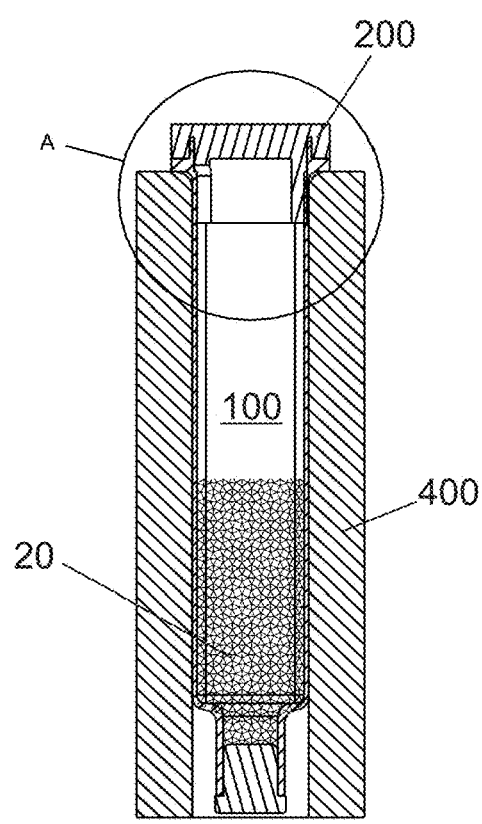
FIG. 46 depicts a seventh step in which the cap is inserted into the syringe barrel to its second, sealing position.
Figure 47:
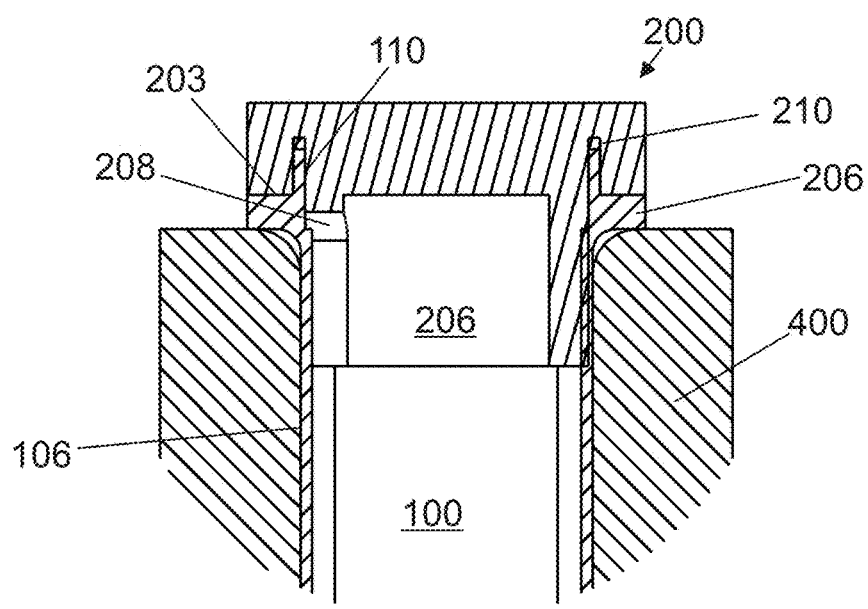
FIG. 47 is an expanded view of the objects of FIG. 46 at location A.

In FIG. 44, sublimation of product 10 has been completed so as to produce lyophilized product 20. Block 400 and syringe assembly 300 contained therein are returned to a vertical orientation in a fifth step of the method of the present invention depicted in FIG. 45. In a sixth step of the method, cap 200 is inserted fully into syringe barrel 100 as depicted in FIGS. 46 and 47, rim 110 of syringe barrel 100 being positioned within slot 210 of cap 200, and slot 208 of cap 200 being covered so as to seal lyophilized product 20 within syringe assembly 300.

Figure 48:
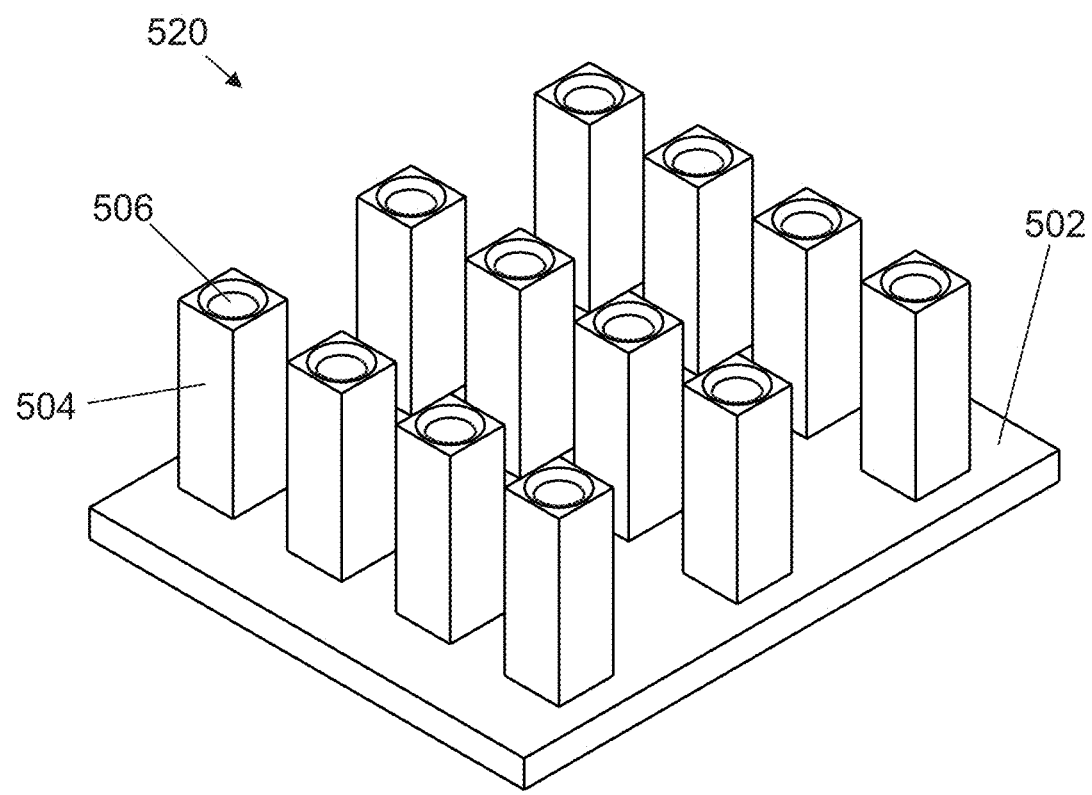
FIG. 48 depicts an ejector plate for use with the thermal block of FIG. 31.
Figure 49:
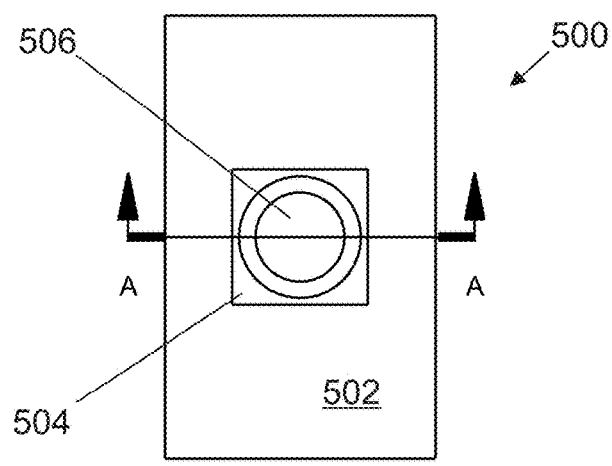
FIG. 49 is a plan view of a segment of the ejector plate of FIG. 48 containing a single upright, hereinafter used to depict subsequent steps of a lyophilizing method of the present invention.
Figure 50:
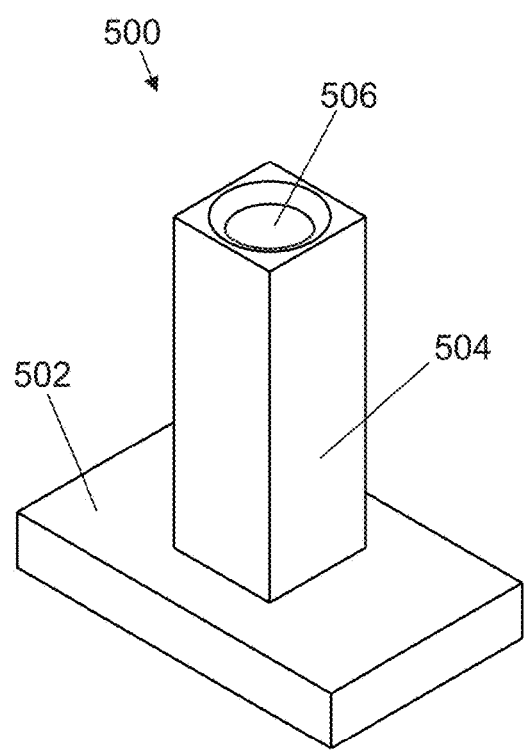
FIG. 50 is a perspective view of the objects of FIG. 49.
Figure 51:
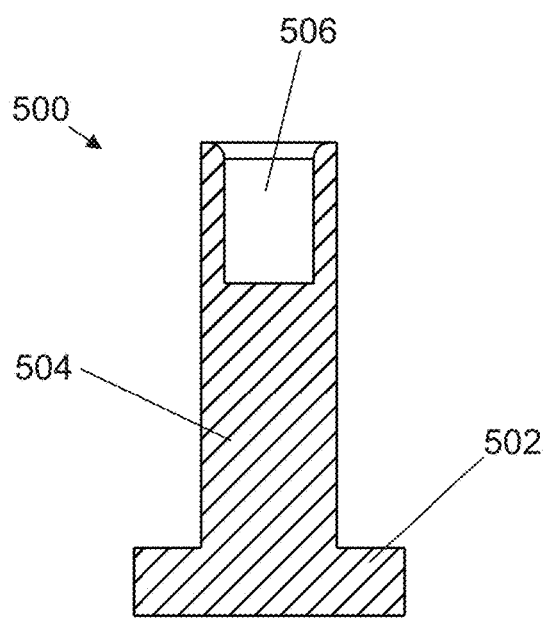
FIG. 51 is a sectional view of the objects of FIG. 49 at location A-A.
Figure 52:
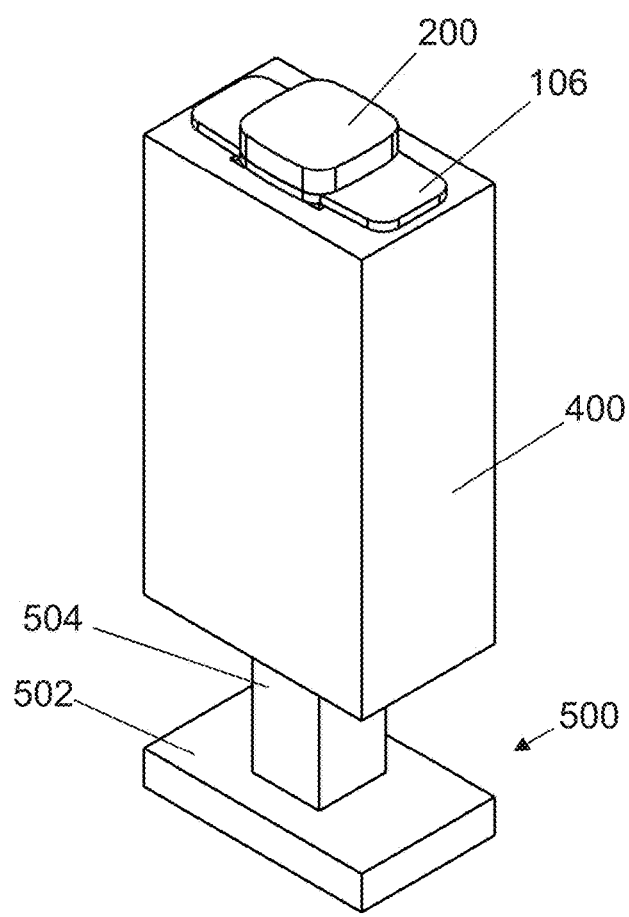
FIG. 52 is an upper perspective view of an eighth step in the method of the present invention wherein the block and syringe barrel are positioned on the upright of the ejector segment of FIG. 49.
Figure 53:
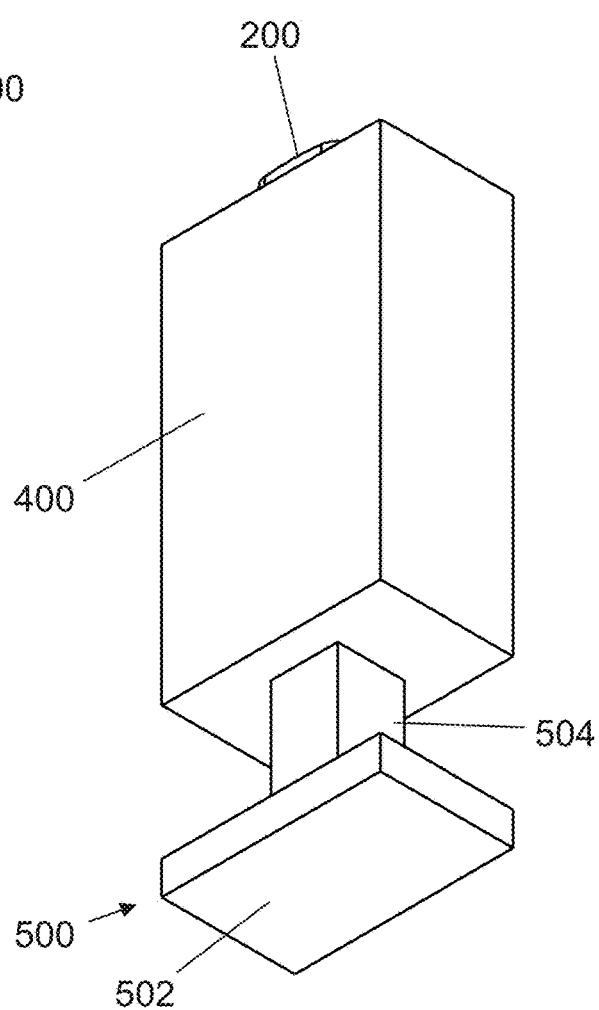
FIG. 53 is a lower perspective view of the objects of FIG. 52.

FIG. 48 depicts an ejector plate 520 that may be used to assist in the removal of the plurality of syringes 300 from the wells of block 420 (FIGS. 31 through 33). Ejector plate 520 has a planar base 502 from which protrude vertical portions 504. Vertical portions 504 have formed in their top surface's recesses 506, recesses 506 being configured to accommodate distal portions 114 of syringe barrel 100, and stopper 250 positioned therein. FIGS. 49 through 51 depict a segment 500 of ejector plate 520 containing a single vertical portion 504. Hereinafter the function of ejector plate 520 will be described using segment 500. For simplicity, segment 500 of ejector plate 520 will be referred to as "ejector 500" in the following descriptions. It will be understood that descriptions of the ejector functions so described are applicable to all segments of ejector plate 520.

Figure 56:
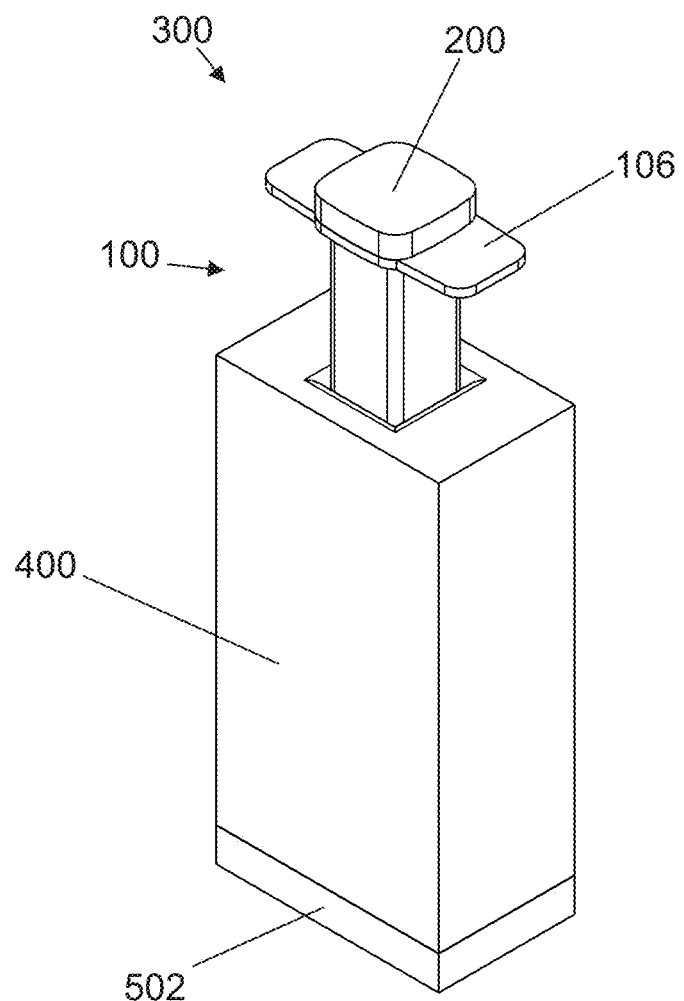
FIG. 56 is a perspective view of a ninth step in the method of this invention in which the syringe barrel is partially ejected from the block segment.
Figure 57:
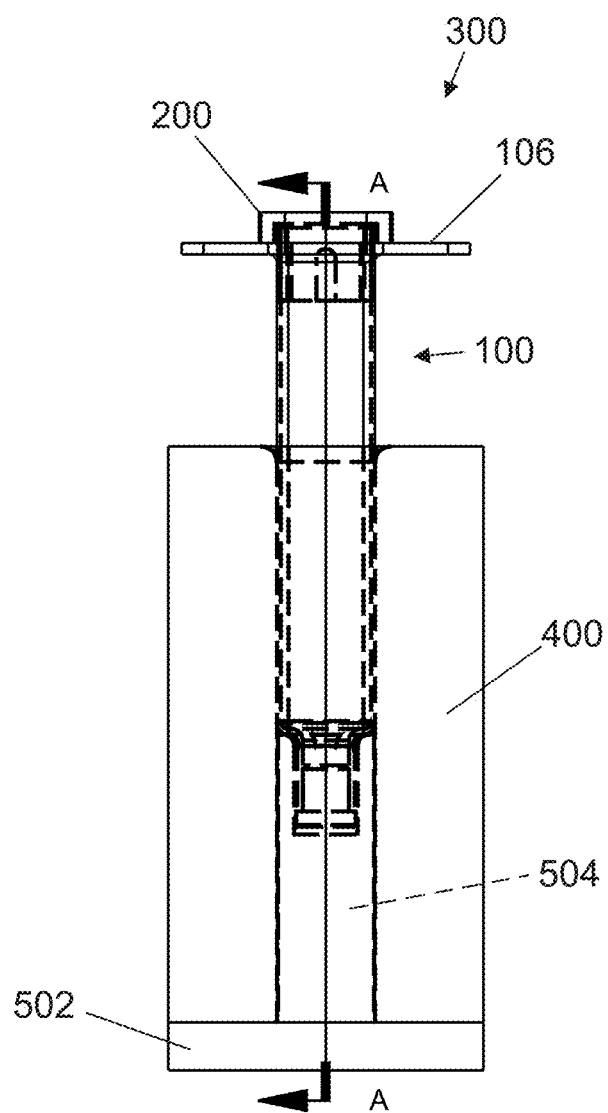
FIG. 57 is a side elevational view of the objects of FIG. 56.
Figure 58:
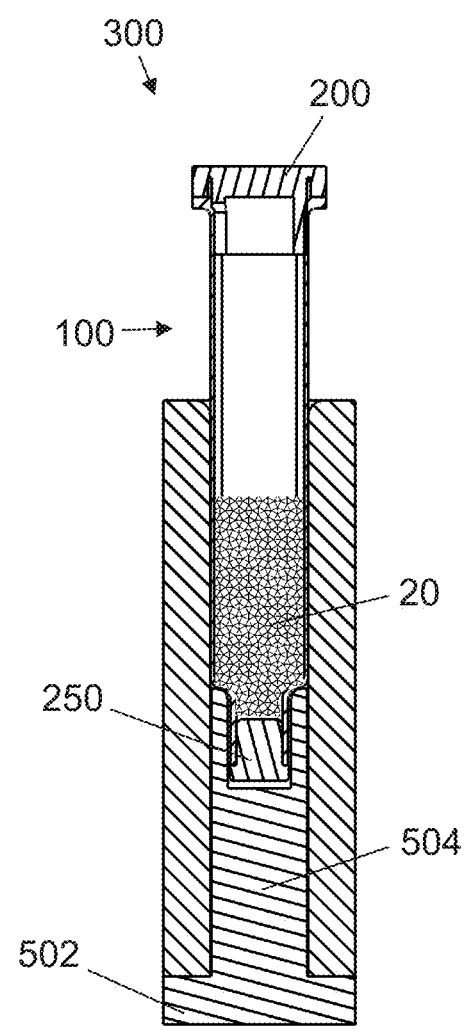
FIG. 58 is a sectional view of the objects of FIG. 57 at location A-A.

Block 400 with syringe assembly 300 therein may be positioned on ejector 500 as depicted in FIGS. 52 through 55. Moving block 400 downward as depicted in FIGS. 56 through 58 causes syringe assembly 300 to be partially dislodged from block 400 so as to allow easy manual removal of syringe assembly 300 from block 400.

Figure 59:
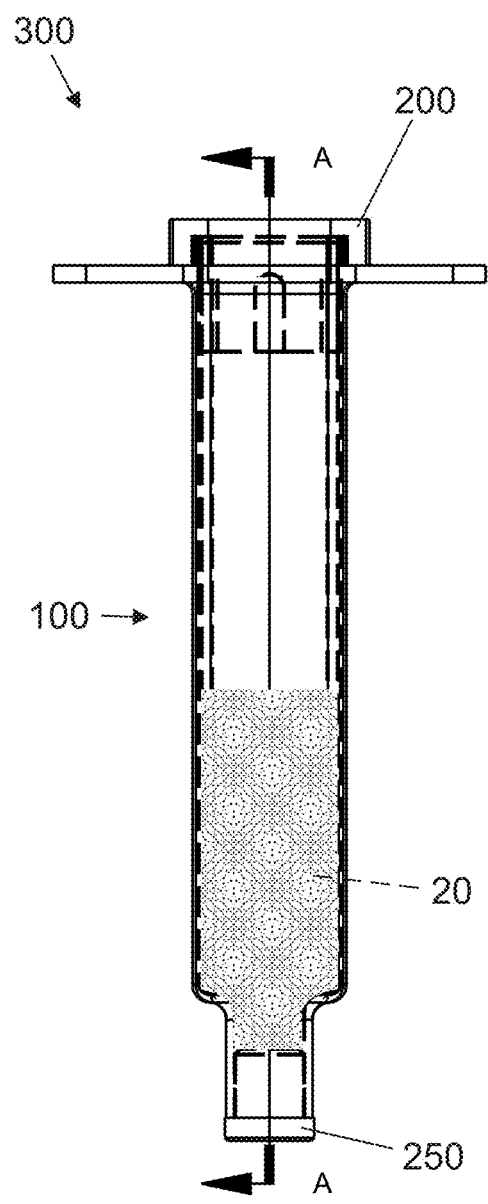
FIG. 59 depicts a syringe barrel of the present invention with lyophilized material formed using methods of the present invention.
Figure 60:
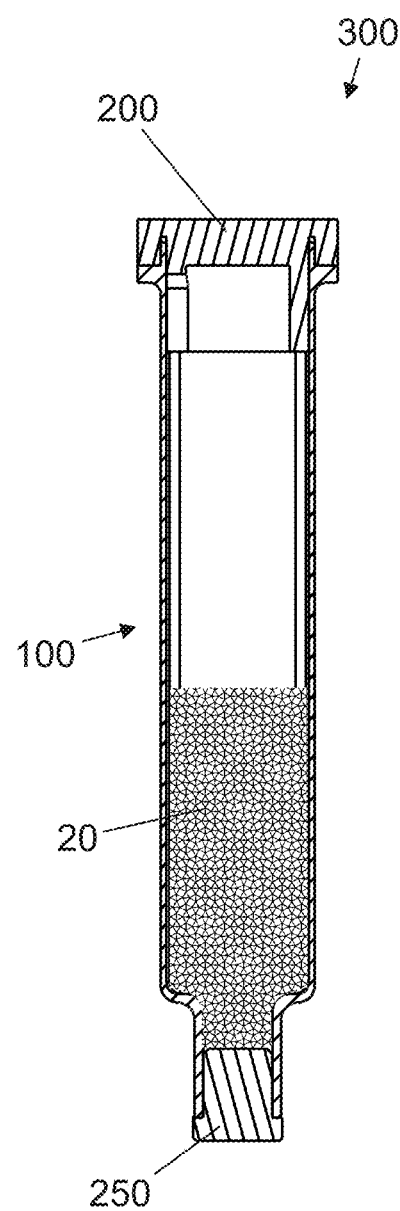
FIG. 60 is a sectional view of the objects of FIG. 59 at location A-A.

FIGS. 59 and 60 depict lyophilized product 20 in sealed syringe assembly 300 at the completion of lyophilization using methods and devices of the present invention.

In methods and devices previously herein described, at completion the product is contained in a syringe assembly sealed with a cap. Before use of the product, the cap must be removed and a diluent added to the syringe for reconstitution of the lyophilized product. Thereafter, a combination of piston and plunger may be inserted into the syringe body and the medication may be administered to the patient. In other methods of the present invention the lyophilized product is contained within a syringe wherein the piston component is already in place and provides the proximal seal. This is advantageous as it minimizes steps required before administration of the product with their associated potential for compromised product or wastage.

An exemplary method for producing lyophilized product in a syringe ready for solubilization and administering to a patient is hereafter described.

Figure 61:
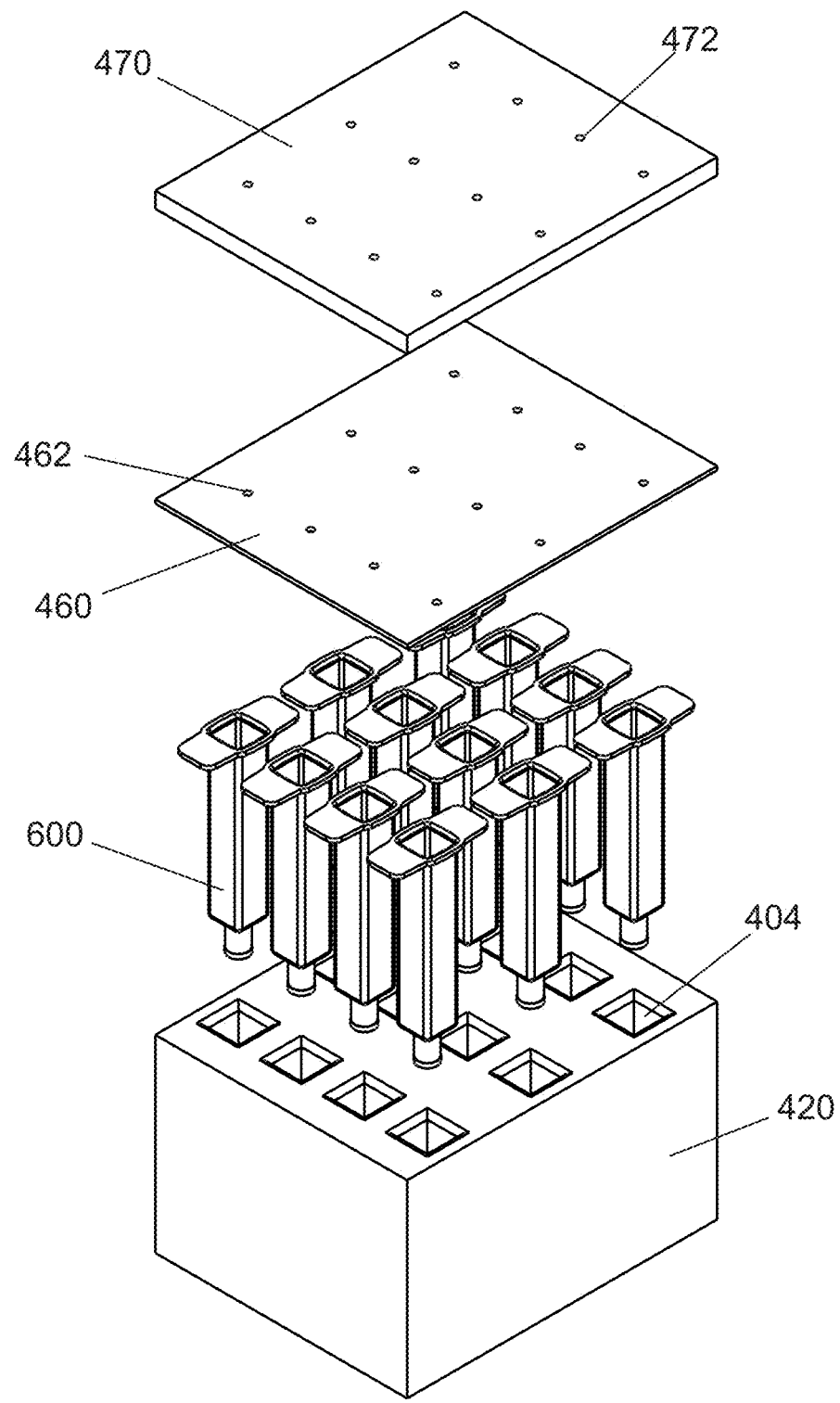
FIG. 61 is a perspective view of an exploded assembly used in an alternate embodiment lyophilization method of the present invention.
Figure 62:
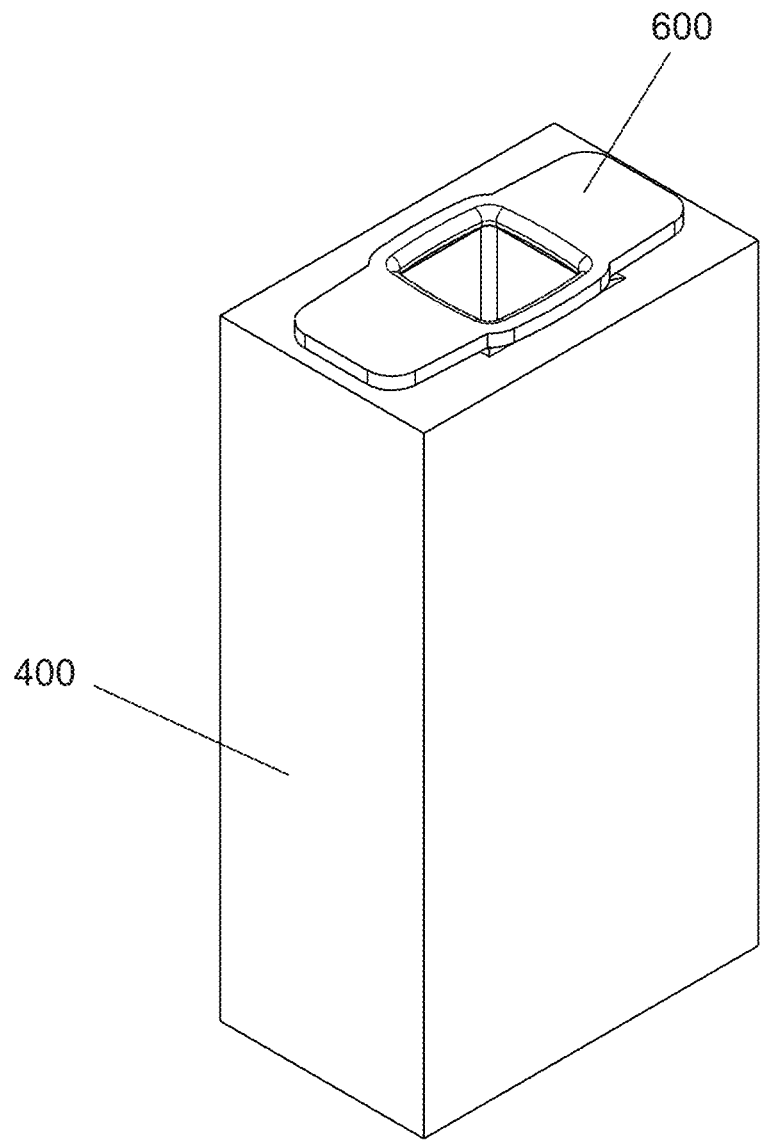
FIG. 62 depicts a second syringe barrel of the present invention containing fluid for lyophilization is inserted into a thermal block segment in a first step of a lyophilization method of the present invention.
Figure 63:
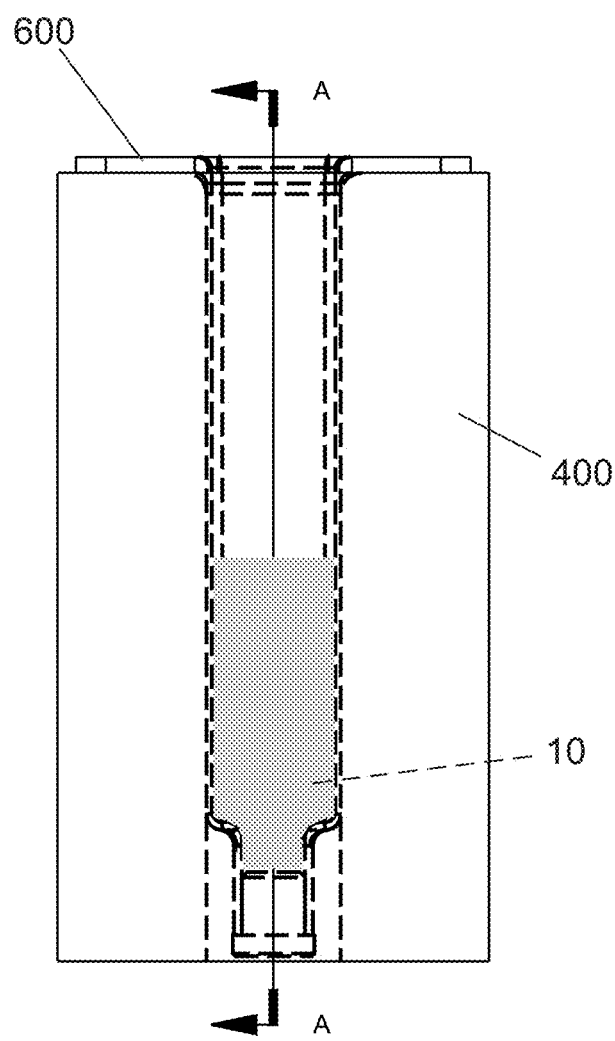
FIG. 63 is a side elevational view of the objects of FIG. 62.
Figure 64:
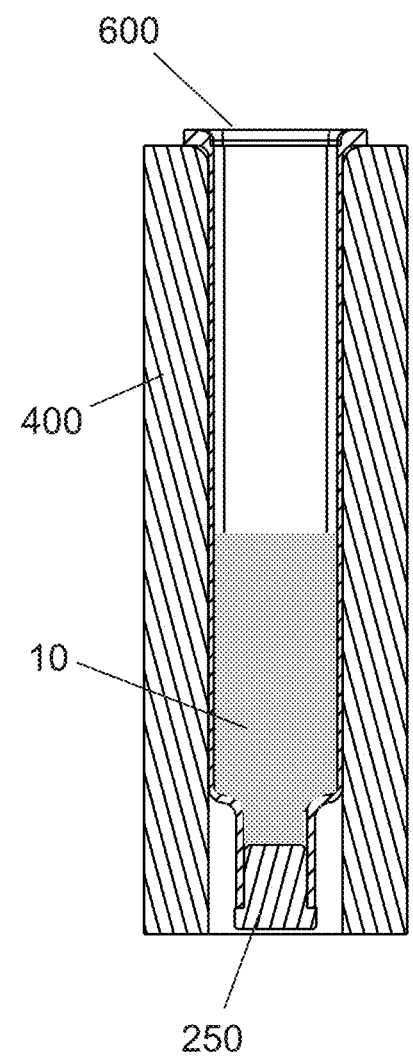
FIG. 64 is a sectional view of the objects of FIG. 63 at location A-A.
Figure 65:
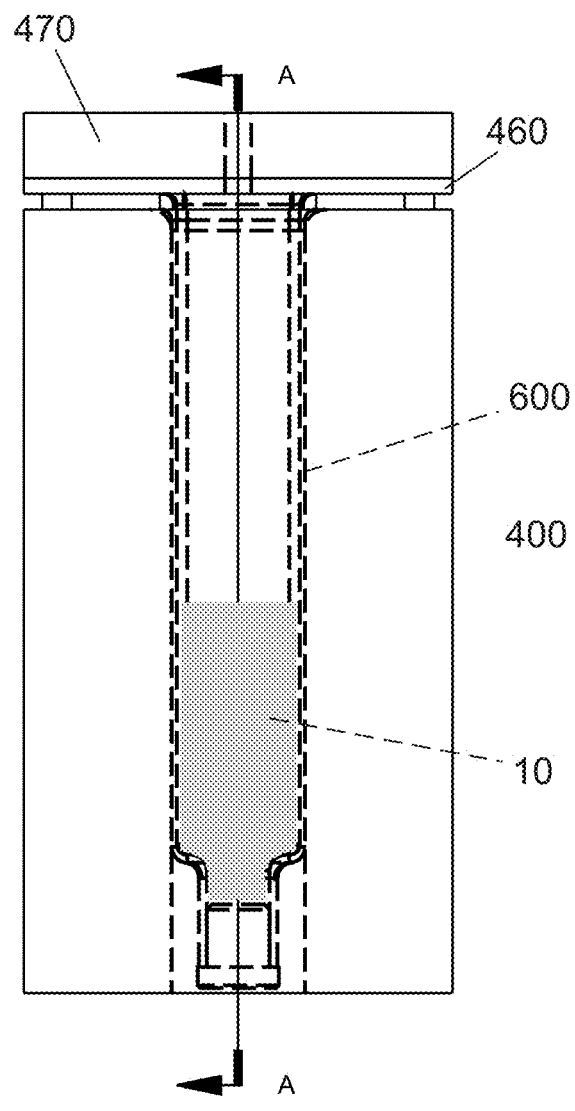
FIG. 65 depicts a second step of the method wherein a gasket and plate are positioned on the thermal block segment.
Figure 66:
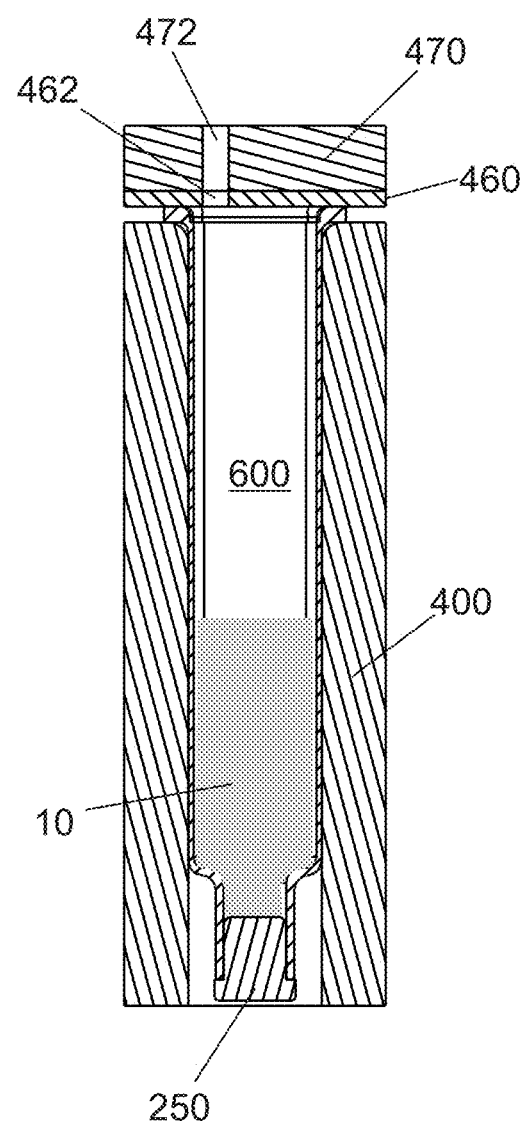
FIG. 66 is a sectional view of the objects of FIG. 65 at location A-A.
Figure 67:
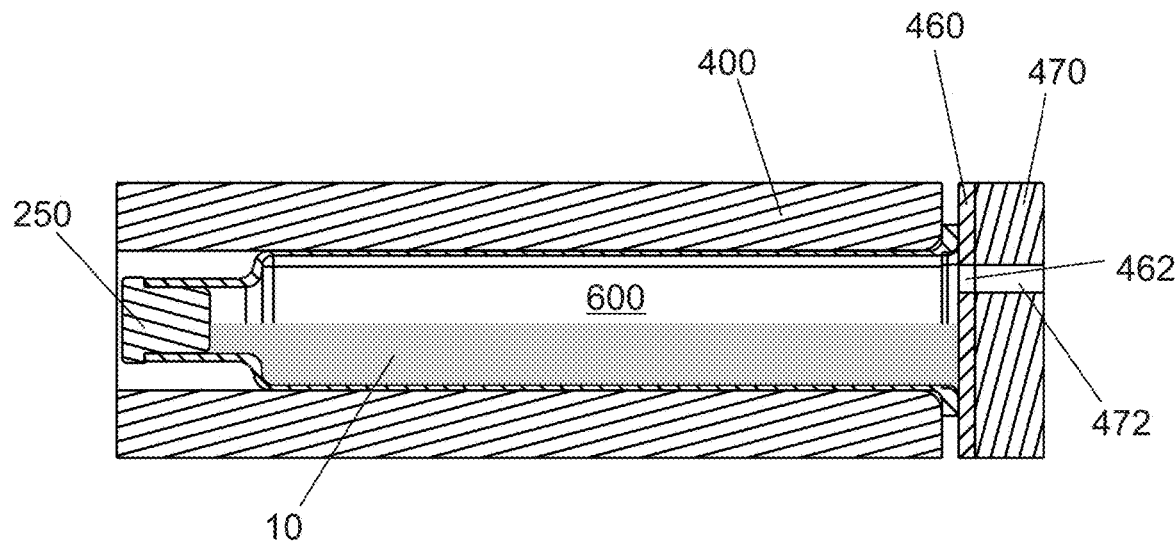
FIG. 67 depicts a third step in which the objects of FIG. 65 are reoriented in a horizontal position.
Figure 68:
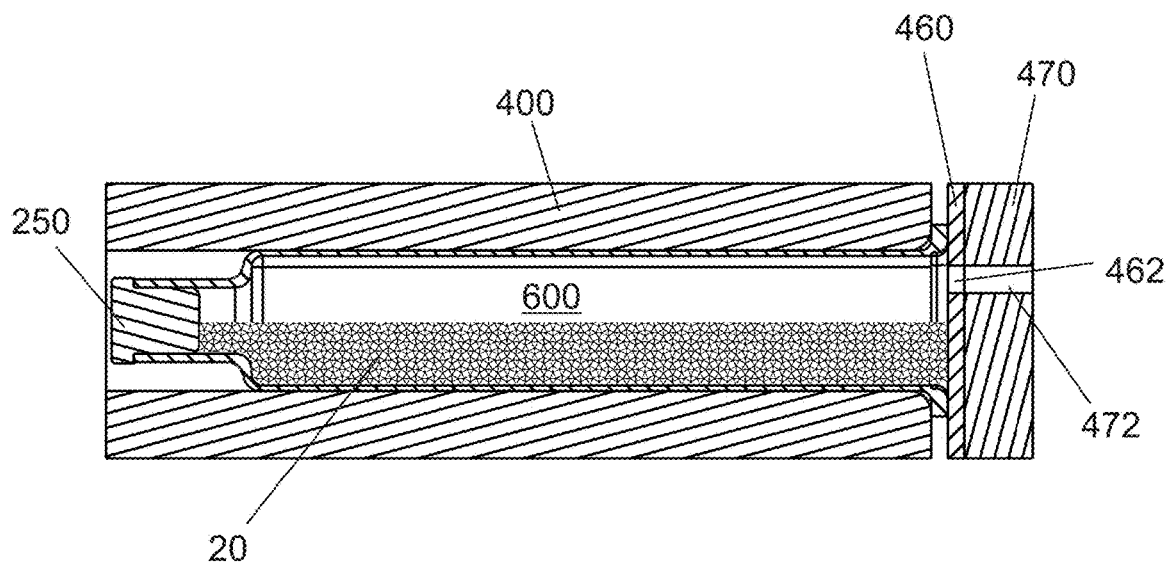
FIG. 68 depicts a fourth step in which the fluid has been fully lyophilized.
Figure 69:
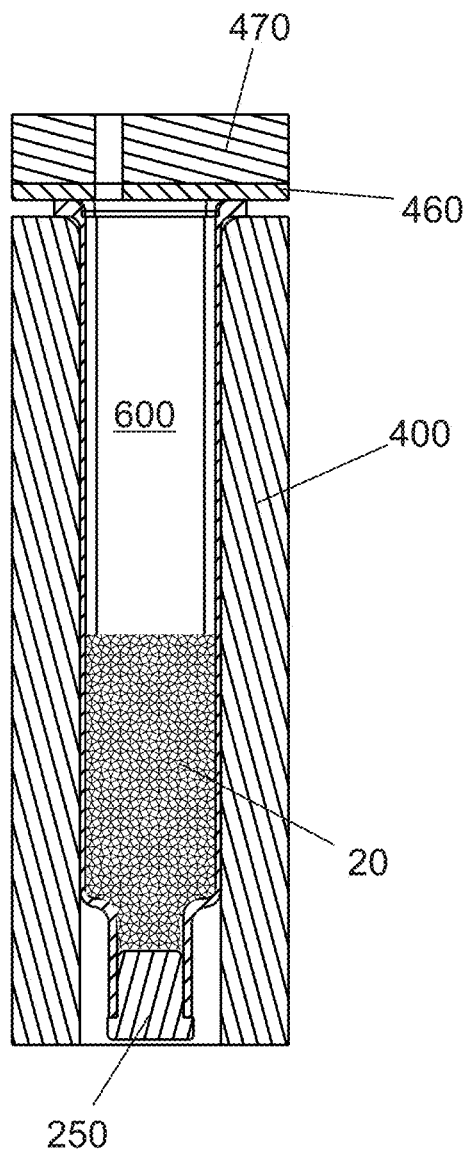
FIG. 69 depicts a fifth step in which the syringe barrel and block have been returned to a vertical position.
Figure 70:
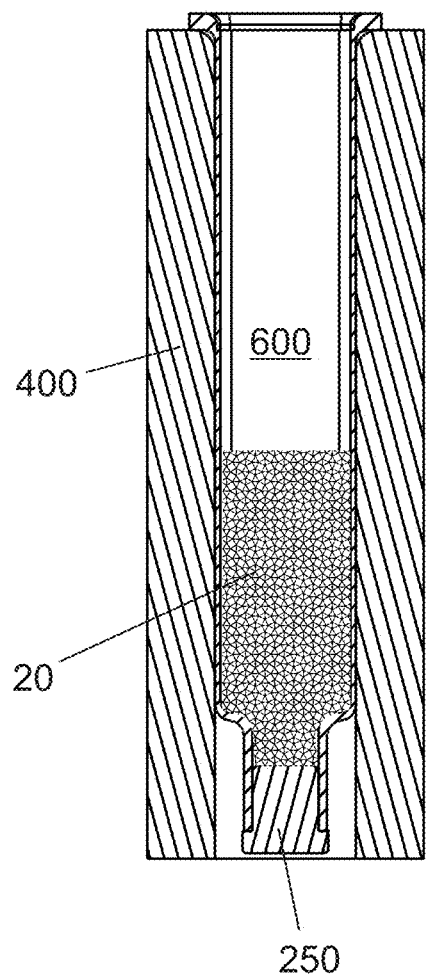
FIG. 70 depicts a sixth step in which the plate and gasket have been removed.
Figure 71:
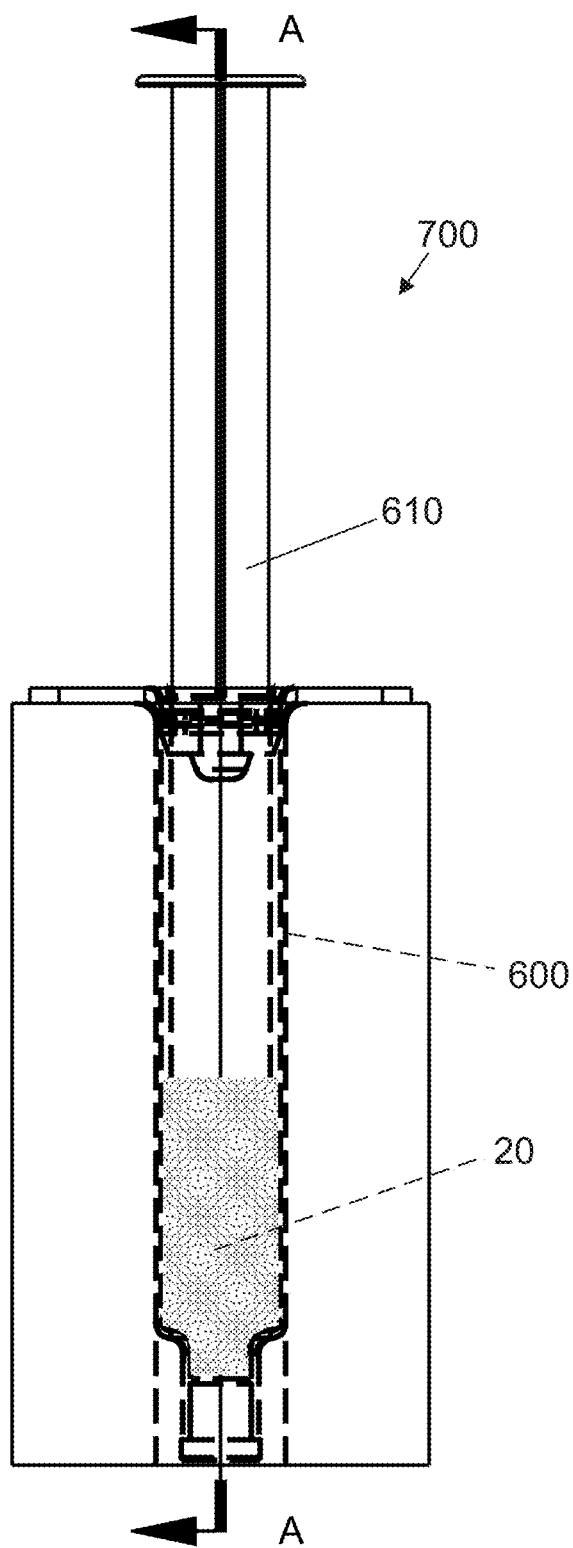
FIG. 71 depicts a seventh step in the lyophilization method in which a plunger is inserted into the syringe barrel until the plunger seal seals the material within the plunger barrel.
Figure 72:
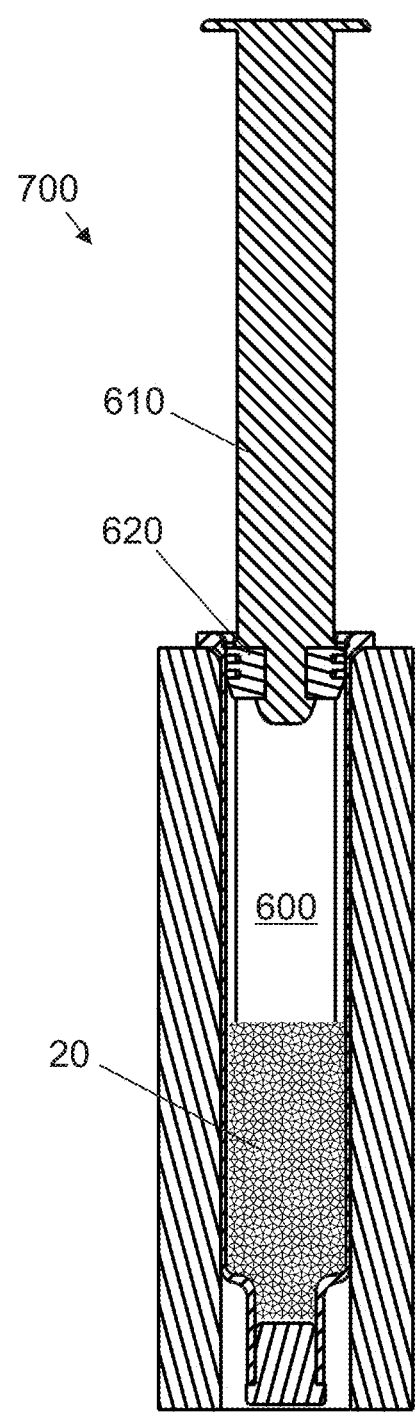
FIG. 72 is a sectional view of the objects of FIG. 71 at location A.
Figure 75:
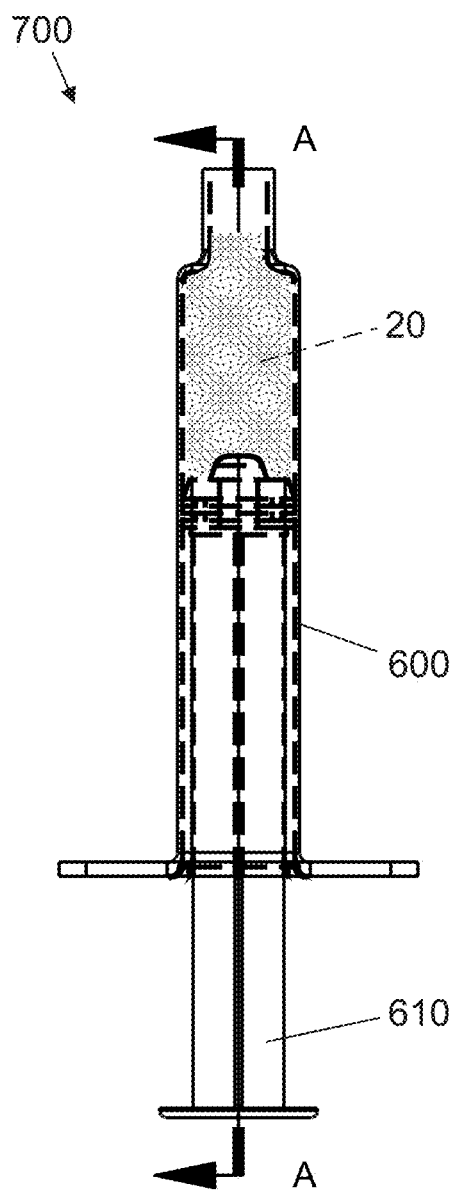
FIG. 75 depicts a ninth step in which the distal stopper is removed and the plunger is advanced with the distal end elevated.
Figure 76:
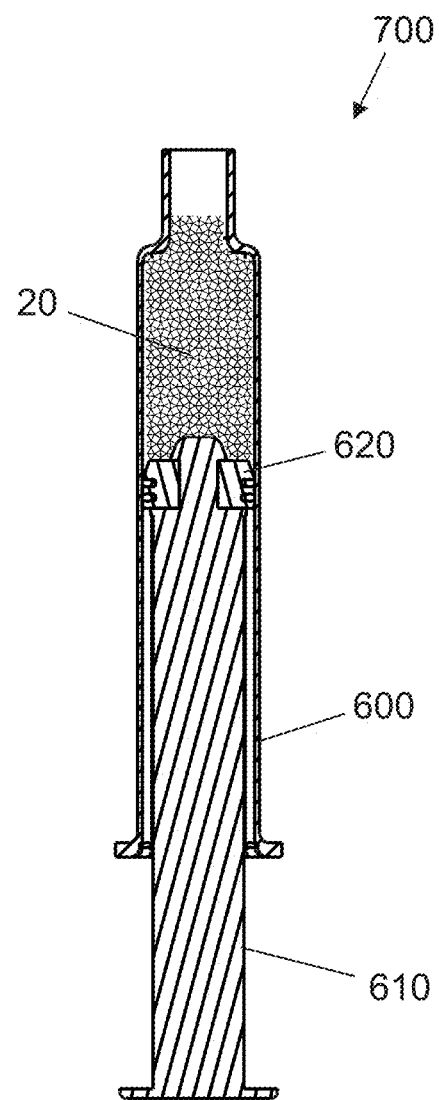
FIG. 76 is a sectional view of the objects of FIG. 75 at location A-A.
Figure 77:
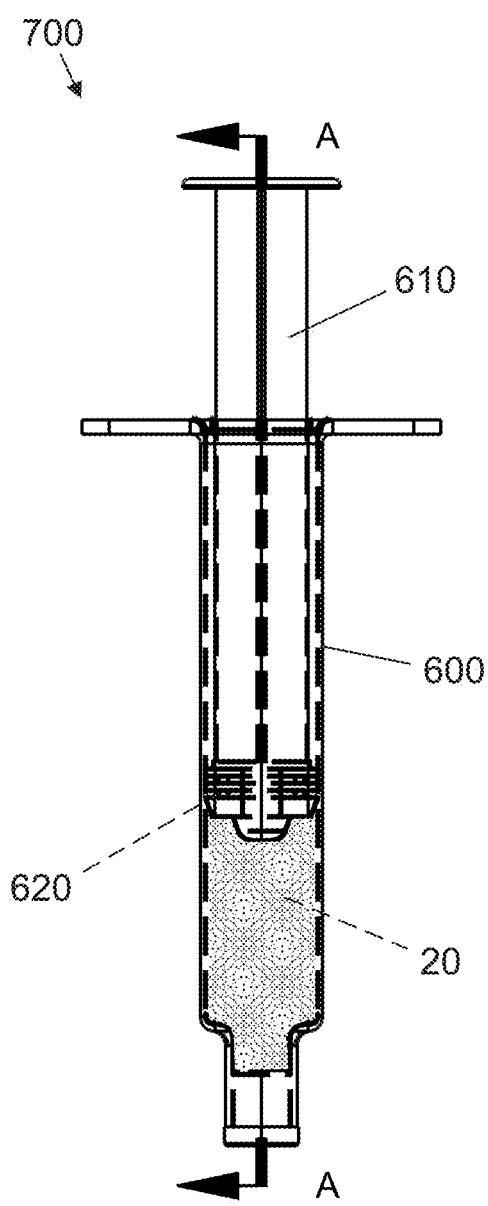
FIG. 77 depicts a syringe of the present invention wherein is formed lyophilized material using methods of the present invention.
Figure 78:
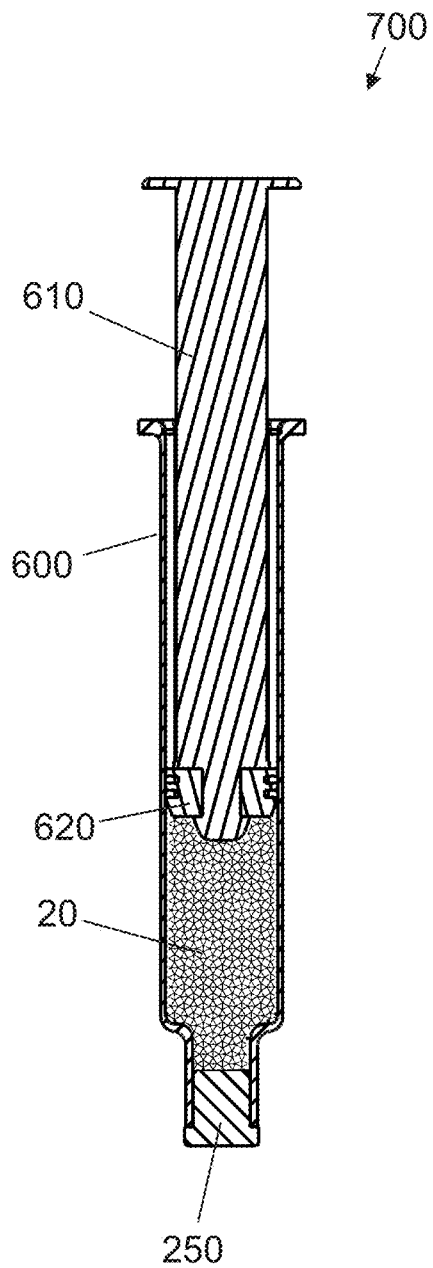
FIG. 78 is a sectional view of the objects of FIG. 77 at location A-A.

FIG. 61 depicts elements of a system for lyophilizing product in a syringe assembly wherein at completion the product is contained in a syringe with plunger, ready for solubilization and administering to a patient. A plurality of syringe barrels 600 are inserted into block 420. Thereafter, gasket 460 with openings 462 and plate 470 with openings 472 are affixed to block 420 by a suitable securing method, not shown. Hereafter details of the method will be described as previously done using block segment 400 and syringe body 600 positioned therein. Syringe barrel 600 is identical to syringe barrel 100 (FIGS. 1 through 7) in all aspects of form and function except as specifically subsequently specified, namely rim 110 is eliminated. FIGS. 62 through 64 depict a first step in a lyophilization method of the present embodiment wherein syringe barrel 600 containing product 10 for lyophilization is inserted into block 400. In a second step, gasket 460 and plate 470 are affixed to block 400 wherein aligned openings 462 and 472 are offset from the axis of barrel 600 as shown in FIG. 66. Block 400 with syringe barrel 600 positioned therein and plate 470 and gasket 460 affixed thereto is reoriented to a horizontal position as depicted in FIG. 67 in a third step of the method. Aligned openings 462 and 472 provide a path for venting during sublimation of product 10. In FIG. 68, sublimation is complete and liquid product 10 has become lyophilized product 20. Thereafter, in a fourth step of the method, block 400 with syringe barrel 600 containing product 20 and gasket 460 and plate 470 affixed thereto is reoriented to the vertical position as depicted in FIG. 69. Plate 470 and gasket 460 are then removed in a fifth step of the method after which block 400, syringe barrel 600 and product 20 are as shown in FIG. 70. Syringe plunger 630 with piston seal 640 is then assembled to syringe body 600 as depicted in FIGS. 71 and 72 in a sixth step of the method to create syringe assembly 700. Plunger 630 is inserted until seal 640 of plunger 630 effectively seals off the interior of syringe barrel 600 and product 20 contained therein from outside contamination. Syringe assembly 600 is then partially ejected from block 400 using ejector 500 in the manner previously herein described (FIGS. 73 and 74) after which sealed syringe assembly 600 is removed manually (seventh step). Thereafter syringe assembly 700 is reoriented as depicted in FIGS. 75 and 76 and stopper 250 is removed. Plunger 630 is then advanced to remove excess air from syringe assembly 700, after which stopper 250 is reinserted. FIGS. 77 and 78 depict lyophilized product 20 in syringe assembly 700 ready for the addition of a diluent and administration to a patient. Because product 20 is lyophilized, special storage conditions are not required.

INDUSTRIAL APPLICABILITY

As discussed above, lyophilization is ubiquitous in the chemical, pharmaceutical, and food industries. However, there is an ongoing need in the art to improve the efficiency and economy of the lyophilization process. The instant invention addresses this continuing need by providing a readily scalable lyophilization assembly, apparatus and method that imparts a shorter lyophilization cycle timeline and affords uniformity in all units of a lyophilization batch.

While the invention is herein described in detail and with reference to specific embodiments thereof, it is to be understood that the foregoing description is exemplary and explanatory in nature and is intended to illustrate the invention and its preferred embodiments. Through routine experimentation, one skilled in the art will readily recognize that various changes and modifications can be made therein without departing from the spirit and scope of the invention. For example, this disclosure includes and contemplates combinations with features and elements known to the average artisan in the art. Thus, the novel embodiments, features, and elements that have been disclosed may also be combined with any conventional features or elements to form a distinct invention as defined by the claims. Likewise, any feature or element of any embodiment may also be combined with features or elements from other inventions to form another distinct invention as defined by the claims. Therefore, it will be understood that any of the features shown and/or discussed in the present disclosure may be implemented singularly or in any suitable combination.

Other advantages and features will become apparent from the claims filed hereafter, with the scope of such claims to be determined by their reasonable equivalents, as would be understood by those skilled in the art. Thus, the invention is intended to be defined not by the above description, but by the following claims and their equivalents.

All publications, patent applications, patents and other references mentioned herein are incorporated by reference in their entirety. However, nothing herein should be construed as an admission that the invention is not entitled to antedate such disclosure by virtue of prior invention.

What is claimed:

1. A lyophilization apparatus, said apparatus comprising:
   a. a thermal block made from a single piece of heat conductive material and characterized by a top side, a bottom side, and a medial thickness extending therebetween, wherein said block is provided with a plurality of uniform wells arranged on said top side and extending a predetermined depth into said medial thickness, further wherein each of said plurality of wells is configured to receive a single container, and
   b. one or more containers, wherein each container is characterized by resiliently deformable lateral walls defining an exterior surface, a hollow interior configured to retain a product in its initial and lyophilized forms, and a proximal opening;
   wherein each well is sized and shaped to closely accommodate one of said one or more containers, whereby insertion of said one container into its respective well causes the lateral walls of said container to deform and the exterior surface of said container to be compressed into substantial intimate contact with an inner wall of the respective well.

2. The apparatus of claim 1, wherein said heat conductive material is metal.

3. The apparatus of claim 1, wherein said plurality of uniform wells extend through the medial thickness of said block such that each well is comprised of a proximal opening disposed in the top side of said block and a distal exit disposed in the bottom side of said block.

4. The apparatus of claim 1, wherein said one or more containers are fabricated from a resilient polymer.

5. The apparatus of claim 1, wherein said one or more containers comprise a vial or ampoule.

6. The apparatus of claim 1, wherein said one or more containers comprise a dispensing syringe.

7. The apparatus of claim 6, wherein each dispensing syringe is comprised of an elongate central barrel having a hollow bore configured to retain said product to be lyophilized, an open distal tip configured to engage a hypodermic needle assembly, and said proximal opening is configured to receive a sealing piston and dispensing plunger.

8. The apparatus of claim 7, wherein said central barrel has a substantially square cross-section characterized by four elongate side panels.

9. The apparatus of claim 8, wherein each of said side panels bow outward to form a convex exterior surface that compresses against the inner wall of its respective well.

10. The apparatus of claim 7, wherein the proximal end of said central barrel is further characterized by a wide radial flange that rests against said proximal well opening so as to prevent vertical displacement of the syringe from its respective well.

11. The apparatus of claim 7, wherein said open distal tip is sealed by a distal stopper.

12. The apparatus of claim 11, wherein said open distal tip comprises a Luer taper and said distal stopper comprises a Luer cap.

13. A lyophilization assembly comprising:
   a. the apparatus of claim 1 in which said one or more containers are each inserted into a respective well; and
   b. a means for alternatively sealing and venting the respective hollow interiors of said one or more containers.

14. The lyophilization assembly of claim 13, further comprising:
   c. an ejector plate to assist in the removal of said one or more containers from said thermal block, said ejector plate comprising a planar base having a plurality of vertical portions protruding therefrom, wherein said vertical portions are identical in number and spatial orientation to that of said plurality of wells such that moving said block-container apparatus downward onto said vertical portions causes said containers to be dislodged from their respective wells.

15. The lyophilization assembly of claim 14, wherein said means for alternatively sealing and venting the respective interiors of said one or more containers comprises a series of container caps, each of which is removably mounted to the proximal opening of a corresponding container, whereby when said cap is partially inserted into said proximal opening, a passage for gaseous outflow from the container interior is formed, thereby providing an escape path for outgassing during the lyophilization process, further wherein said passage is closed when said cap is fully inserted into said proximal opening, such that said lyophilized product is sealed within said container interior.

16. The lyophilization assembly of claim 14, wherein said means for alternatively sealing and venting the respective interiors of said one or more containers comprises (a) a sealing member configured to cover the top side of the block and the plurality of wells, the sealing member having a first venting mechanism configured to allow vapors to escape from said one or more containers, and (b) a plate configured to secure the sealing member to the block, the plate having a second venting mechanism configured to allow the vapors received through the first mechanism to escape.

17. The lyophilization assembly of claim 16, wherein said sealing member comprises a silicone pad provided with a series of apertures that serve as a said first venting mechanism.

18. The lyophilization assembly of claim 17, wherein said seconding venting mechanism comprises a series of perforations in said plate, whereby said plate perforations align with said silicone pad apertures.

19. The lyophilization assembly of claim 18, wherein said plate perforations and said silicone pad apertures are aligned with but offset from the axis of the respective proximal openings.

20. A method for lyophilizing a product using the lyophilization assembly of claim 13, said method comprising the steps of:
   a. positioning said thermal block in an upright position and placing each of said one or more containers into its respective well such that the proximal opening of each container faces up;
   b. via the respective proximal openings, filling each container with said product to be lyophilized;
   c. engaging said means for sealing and venting the respective hollow interiors of said one or more containers so as to allow vapors to escape from said one or more containers while preventing product from leaking;

d. optionally rotating the lyophilization assembly from a vertical configuration, wherein said proximal openings face up, to a horizontal configuration, wherein proximal openings face sideways, so as to enhance the efficiency of the lyophilization process; and e. applying heat to said thermal block until all water is removed from said product to be lyophilized.

* * * * *